(12) United States Patent
Chae et al.

(10) Patent No.: US 8,841,069 B2
(45) Date of Patent: Sep. 23, 2014

(54) DENDRON-MEDIATED DNA VIRUS DETECTION

(75) Inventors: Chi-Bom Chae, Seoul (KR); Kyung-Tae Kim, Seoul (KR); Seong-Suk Hur, Seoul (KR)

(73) Assignee: Korea Materials & Analysis Corporation, Daejeon (KR)

( * ) Notice: Subject to any disclaimer, the term of this patent is extended or adjusted under 35 U.S.C. 154(b) by 500 days.

(21) Appl. No.: 12/036,247

(22) Filed: Feb. 23, 2008

(65) Prior Publication Data

US 2009/0253120 A1 Oct. 8, 2009

Related U.S. Application Data

(63) Continuation-in-part of application No. 11/616,761, filed on Dec. 27, 2006.

(60) Provisional application No. 60/755,503, filed on Dec. 29, 2005.

(51) Int. Cl.
*C12Q 1/68* (2006.01)
*C12Q 1/70* (2006.01)

(52) U.S. Cl.
CPC .................................... *C12Q 1/708* (2013.01)
USPC ................... 435/5; 435/6; 435/6.1; 435/6.11; 435/6.12

(58) Field of Classification Search
None
See application file for complete search history.

(56) References Cited

U.S. PATENT DOCUMENTS

| | | | |
|---|---|---|---|
| 5,750,347 A | 5/1998 | Bagasra et al. | |
| 6,280,930 B1 * | 8/2001 | Backus et al. | 435/6.18 |
| 7,138,121 B2 * | 11/2006 | Spangler et al. | 424/178.1 |
| 2003/0039957 A1 | 2/2003 | McCarthy et al. | |
| 2004/0023248 A1 * | 2/2004 | O'Malley | 435/6 |
| 2004/0029258 A1 * | 2/2004 | Heaney et al. | 435/287.2 |
| 2005/0037413 A1 | 2/2005 | Park | |
| 2007/0190537 A1 * | 8/2007 | Park et al. | 435/6 |
| 2008/0008990 A1 * | 1/2008 | Chae et al. | 435/5 |
| 2008/0064070 A1 * | 3/2008 | Park et al. | 435/91.2 |
| 2009/0215050 A1 * | 8/2009 | Jenison | 435/6 |

FOREIGN PATENT DOCUMENTS

| | | | |
|---|---|---|---|
| EP | 1 201 771 A2 * | 2/2002 | C12Q 1/70 |
| WO | WO 96/31622 | 10/1996 | |
| WO | WO 01/48242 | 7/2001 | |
| WO | WO 02/20469 A1 * | 3/2002 | |
| WO | WO 2004/020667 | 3/2004 | |
| WO | WO 2004/079002 | 9/2004 | |
| WO | WO 2005/075680 | 8/2005 | |
| WO | WO 2007/079129 | 7/2007 | |
| WO | WO 2007/119066 | 10/2007 | |

OTHER PUBLICATIONS

Huber et al., Accessing Single Nucleotide Polymorphisms in Genomic DNA by Direct Multiplex Polymerase Chain Reaction Amplification on Oligonucleotide Microarrays, Analytical Biochemistry 303, 25-33 (2002).*
Hong et al., Self-Assembly of a Dendron through Multiple Ionic Interaction to Give Mesospacing between Reactive Amine Groups on the Surface, Langmuir 2003, 19, 2357-2365.*
Auroux et al., Miniaturised nucleic acid analysis, M i n i a t u r i s a t ion for C h e m i s t r y, B iology & Bioengi n e e r ing, Lab Chip, 2 0 0 4, 4, pp. 534-546, First published as an Advance Article on the web Oct. 22, 2004.*
Kajiyama et al., Genotyping on a Thermal Gradient DNA Chip,Genome Res. 2003 13: 467-475.*
Oh et al. (DNA microarrays on a dendron-modified surface improve significantly the detection of single nucleotide variations in the p53 gene, Nucleic Acids Research, 2005, vol. 33, No. 10, Jun. 6, 2005).*
Guo et al. (Direct fluorescence analysis of genetic polymorphisms by hybridization with oligonucleotide arrays on glass supports, Nucleic Acids Research, 1994, vol. 22, No. 24, pp. 5456-5465).*
Trau et al., Anal. Chem., 74:3168-3173 (2002).
Benters et al., Nucl. Acids Res., 30(2):e10 (2002).
Huber et al., Anal. Biochem., 303(25-33) (2002).
Hong et al., Langmuir, 19:2357-2365 (2003).
Bell et al., Bioconjugate Chem., 14:488-493 (2003).
Oh et al., Nucl. Acids Res., 33(10):e90 (2005).
Hong et al., Langmuir, 21(10):4257-61 (May 10, 2005).
Hong et al., Nucl. Acids Res., 33(12):e106 (2005).
"FastStart High Fidelity PCR System for the Diagnostic Industry," www.roche-applied-science.com (Jun. 2008), ROCHE.

* cited by examiner

*Primary Examiner* — Christopher M Babic
*Assistant Examiner* — Aaron Priest
(74) *Attorney, Agent, or Firm* — Sughrue Mion, PLLC

(57) ABSTRACT

The disclosure relates to chips containing nucleic acid probes or primers and their use in methods to detect nucleic acid molecules of DNA viruses. The disclosure includes DNA chips with probes immobilized via a dendron-mediated linkage in contact with a thermocycler capable of automatically regulating the temperature, temperature cycle times, and number of temperature cycles of the chips to provide genetic diagnosis in one step.

21 Claims, 10 Drawing Sheets

Top: PCR in tube and hybridization on slide

Bottom: PCR and hybridization on slide

HBV: codon 233, normal and mutants

ATA
GTA
GTG
ATG

```
ACTACAATAATTCATGTATAAAACTAAGGGCGTAACCGAAATCGGTTGAACCGAAACCGGTTAGTATAAA
AGCAGACATTTTATGCACCAAAAGAGAACTGCAATGTTTCAGGACCCACAGGAGCGACCCAGAAAGTTAC
CACAGTTATGCACAGAGCTGCAAACAACTATACATGATATAATATTAGAATGTGTGTACTGCAAGCAACA
GTTACTGCGACGTGAGGTATATGACTTTGCTTTTCGGGATTTATGCATAGTATATAGAGATGGGAATCCA
TATGCTGTATGTGATAAATGTTTAAAGTTTTATTCTAAAATTAGTGAGTATAGACATTATTGTTATAGTT
TGTATGGAACAACATTAGAACAGCAATACAACAAACCGTTGTGTGATTTGTTAATTAGGTGTATTAACTG
TCAAAAGCCACTGTGTCCTGAAGAAAAGCAAAGACATCTGGACAAAAAGCAAAGATTCCATAATATAAGG
GGTCGGTGGACCGGTCGATGTATGTCTTGTTGCAGATCATCAAGAACACGTAGAGAAACCCAGCTGTAAT
CATGCATGGAGATACACCTACATTGCATGAATATATGTTAGATTTGCAACCAGAGACAACTGATCTCTAC
TGTTATGAGCAATTAAATGACAGCTCAGAGGAGGAGGATGAAATAGATGGTCCAGCTGGACAAGCAGAAC
CGGACAGAGCCCATTACAATATTGTAACCTTTTGTTGCAAGTGTGACTCTACGCTTCGGTTGTGCGTACA
AAGCACACACGTAGACATTCGTACTTTGGAAGACCTGTTAATGGGCACACTAGGAATTGTGTGCCCCATC
TGTTCTCAGAAACCATAATCTACCATGGCTGATCCTGCAGGTACCAATGGGGAAGAGGGTACGGGATGTA
ATGGATGGTTTTATGTAGAGGCTGTAGTGGAAAAAAAAACAGGGGATGCTATATCAGATGACGAGAACGA
AAATGACAGTGATACAGGTGAAGATTTGGTAGATTTTATAGTAAATGATAATGATTATTTAACACAGGCA
GAAACAGAGACAGCACATGCGTTGTTTACTGCACAGGAAGCAAAACAACATAGAGATGCAGTACAGGTTC
TAAAACGAAAGTATTTGGTAGTCCACTTAGTGATATTAGTGGATGTGTAGACAATAATATTAGTCCTAGA
TTAAAAGCTATATGTATAGAAAAACAAAGTAGAGCTGCAAAAAGGAGATTATTTGAAAGCGAAGACAGCG
GGTATGGCAATACTGAAGTGGAAACTCAGCAGATGTTACAGGTAGAAGGGCGCCATGAGACTGAAACACC
ATGTAGTCAGTATAGTGGTGGAAGTGGGGGTGGTTGCAGTCAGTACAGTAGTGGAAGTGGGGGAGAGGGT
GTTAGTGAAAGACACACTATATGCCAAACACCACTTACAAATATTTTAAATGTACTAAAAACTAGTAATG
CAAAGGCAGCAATGTTAGCAAAATTTAAAGAGTTATACGGGGTGAGTTTTTCAGAATTAGTAAGACCATT
TAAAAGTAATAAATCAACGTGTTGCGATTGGTGTATTGCTGCATTTGGACTTACACCCAGTATAGCTGAC
AGTATAAAAACACTATTACAACAATATTGTTTATATTTACACATTCAAAGTTTAGCATGTTCATGGGGAA
TGGTTGTGTTACTATTAGTAAGATATAAATGTGGAAAAAATAGAGAAACAATTGAAAAATTGCTGTCTAA
ACTATTATGTGTGTCTCCAATGTGTATGATGATAGAGCCTCCAAAATTGCGTAGTACAGCAGCAGCATTA
TATTGGTATAAAACAGGTATATCAAATATTAGTGAAGTGTATGGAGACACGCCAGAATGGATACAAAGAC
AAACAGTATTACAACATAGTTTTAATGATTGTACATTTGAATTATCACAGATGGTACAATGGGCCTACGA
TAATGACATAGTAGACGATAGTGAAATTGCATATAAATATGCACAATTGGCAGACACTAATAGTAATGCA
AGTGCCTTTCTAAAAAGTAATTCACAGGCAAAAATTGTAAAGGATTGTGCAACAATGTGTAGACATTATA
AACGAGCAGAAAAAAAACAAATGAGTATGAGTCAATGGATAAAATATAGATGTGATAGGGTAGATGATGG
AGGTGATTGGAAGCAAATTGTTATGTTTTTAAGGTATCAAGGTGTAGAGTTTATGTCATTTTAACTGCA
TTAAAAAGATTTTGCAAGGCATACCTAAAAAAAATTGCATATTACTATATGGTGCAGCTAACACAGGTA
AATCATTATTTGGTATGAGTTTAATGAAATTTCTGCAAGGGTCTGTAATATGTTTTGTAAATTCTAAAAG
CCATTTTTGGTTACAACCATTAGCAGATGCCAAAATAGGTATGTTAGATGATGCTACAGTGCCCTGTTGG
AACTACATAGATGACAATTTAAGAAATGCATTGGATGGAAATTTAGTTTCTATGGATGTAAAGCATAGAC
CATTGGTACAACTAAAATGCCCTCCATTATTAATTACATCTAACATTAATGCTGGTACAGATTCTAGGTG
GCCTTATTTACATAATAGATTGGTGGTGTTTACATTTCCTAATGAGTTTCCATTTGACGAAAACGGAAAT
CCAGTGTATGAGCTTAATGATAAGAACTGGAAATCCTTTTTCTCAAGGACGTGGTCCAGATTAAGTTTGC
ACGAGGACGAGGACAAGGAAAACGATGGAGACTCTTTGCCAACGTTTAAATGTGTGTCAGGACAAAATAC
TAACACATTATGAAAATGATAGTACAGACCTACGTGACCATATAGACTATTGGAAACACATGCGCCTAGA
ATGTGCTATTTATTACAAGGCCAGAGAAATGGGATTTAAACATATTAACCACCAAGTGGTGCCAACACTG
GCTGTATCAAAGAATAAAGCATTACAAGCAATTGAACTGCAACTAACGTTAGAAACAATATATAACTCAC
AATATAGTAATGAAAAGTGGACATTACAAGACGTTAGCCTTGAAGTGTATTTAACTGCACCAACAGGATG
TATAAAAAAACATGGATATACAGTGGAAGTGCAGTTTGATGGAGACATATGCAATACAATGCATTATACA
AACTGGACACATATATATTTGTGAAGAAGCATCAGTAACTGTGGTAGAGGGTCAAGTTGACTATTATG
GTTTATATTATGTTCATGAAGGAATACGAACATATTTTGTGCAGTTTAAAGATGATGCAGAAAAATATAG
```

FIG. 10A

```
TAAAAATAAAGTATGGGAAGTTCATGCGGGTGGTCAGGTAATATTATGTCCTACATCTGTGTTTAGCAGC
AACGAAGTATCCTCTCCTGAAATTATTAGGCAGCACTTGGCCAACCACCCCGCCGCGACCCATACCAAAG
CCGTCGCCTTGGGCACCGAAGAAACACAGACGACTATCCAGCGACCAAGATCAGAGCCAGACACCGGAAA
CCCCTGCCACACCACTAAGTTGTTGCACAGAGACTCAGTGGACAGTGCTCCAATCCTCACTGCATTTAAC
AGCTCACACAAAGGACGGATTAACTGTAATAGTAACACTACACCCATAGTACATTTAAAAGGTGATGCTA
ATACTTTAAAATGTTTAAGATATAGATTTAAAAAGCATTGTACATTGTATACTGCAGTGTCGTCTACATG
GCATTGGACAGGACATAATGTAAAACATAAAAGTGCAATTGTTACACTTACATATGATAGTGAATGGCAA
CGTGACCAATTTTTGTCTCAAGTTAAAATACCAAAAACTATTACAGTGTCTACTGGATTTATGTCTATAT
GACAAATCTTGATACTGCATCCACAACATTACTGGCGTGCTTTTGCTTTGCTTTGTGTGCTTTGTGTG
TCTGCCTATTAATACGTCCGCTGCTTTTGTCTGTGTCTACATACACATCATTAATAATATTGGTATTACT
ATTGTGGATAACAGCAGCCTCTGCGTTTAGGTGTTTTATTGTATATATTATATTTGTTTATATACCATTA
TTTTTAATACATACACATGCACGCTTTTAATTACATAATGTATATGTACATAATGTAATTGTTACATAT
AATTGTTGTATACCATAACTTACTATTTTTCTTTTTATTTTCATATATAATTTTTTTTTTGTTTGTT
TGTTTGTTTTTAATAAACTGTTATTACTTAACAATGCGACACAAACGTTCTGCAAAACGCACAAAACGT
GCATCGGCTACCCAACTTTATAAAACATGCAAACAGGCAGGTACATGTCCACCTGACATTATACCTAAGG
TTGAAGGCAAAACTATTGCTGAACAAATATTACAATATGGAAGTATGGGTGTATTTTTGGTGGGTTAGG
AATTGGAACAGGGTCGGGTACAGGCGGACGCACTGGGTATATTCCATTGGGAACAAGGCCTCCCACAGCT
ACAGATACACTTGCTCCTGTAAGACCCCCTTTAACAGTAGATCCTGTGGGCCCTTCTGATCCTTCTATAG
TTTCTTTAGTGGAAGAAACTAGTTTTATTGATGCTGGTGCACCAACATCTGTACCTTCCATTCCCCAGA
TGTATCAGGATTTAGTATTACTACTTCAACTGATACCACACCTGCTATATTAGATATTAATAATACTGTT
ACTACTGTTACTACACATAATAATCCCACTTTCACTGACCCATCTGTATTGCAGCCTCCAACACCTGCAG
AAACTGGAGGGCATTTTACACTTTCATCATCCACTATTAGTACACATAATTATGAAGAAATTCCTATGGA
TACATTTATTGTTAGCACAAACCCTAACACAGTAACTAGTAGCACACCCATACCAGGGTCTCGCCCAGTG
GCACGCCTAGGATTATATAGTCGCACAACACAACAGGTTAAAGTTGTAGACCCTGCTTTTGTAACCACTC
CCACTAAACTTATTACATATGATAATCCTGCATATGAAGGTATAGATGTGGATAATACATTATATTTTC
TAGTAATGATAATAGTATTAATATAGCTCCAGATCCTGACTTTTTGGATATAGTTGCTTTACATAGGCCA
GCATTAACCTCTAGGCGTACTGGCATTAGGTACAGTAGAATTGGTAATAAACAAACACTACGTACTCGTA
GTGGAAAATCTATAGGTGCTAAGGTACATTATTATTATGATTTAAGTACTATTGATCCTGCAGAAGAAAT
AGAATTACAAACTATAACACCTTCTACATATACTACCACTTCACATGCAGCCTCACCTACTTCTATTAAT
AATGGATTATATGATATTTATGCAGATGACTTTATTACAGATACTTCTACAACCCCGGTACCATCTGTAC
CCTCTACATCTTTATCAGGTTATATTCCTGCAAATACAACAATTCCTTTTGGTGGTGCATACAATATTCC
TTTAGTATCAGGTCCTGATATACCCATTAATATAACTGACCAAGCTCCTTCATTAATTCCTATAGTTCCA
GGGTCTCCACAATATACAATTATTGCTGATGCAGGTGACTTTATTTACATCCTAGTTATTACATGTTAC
GAAAACGACGTAAACGTTTACCATATTTTTTTCAGATGTCTCTTTGGCTGCCTAGTGAGGCCACTGTCT
ACTTGCCTCCTGTCCCAGTATCTAAGGTTGTAAGCACGGATGAATATGTTGCACGCACAAACATATATTA
TCATGCAGGAACATCCAGACTACTTGCAGTTGGACATCCCTATTTTCCTATTAAAAAACCTAACAATAAC
AAAATATTAGTTCCTAAAGTATCAGGATTACAATACAGGGTATTTAGAATACATTTACCTGACCCCAATA
AGTTTGGTTTTCCTGACACCTCATTTATAATCCAGATACACAGCGGCTGGTTTGGGCCTGTGTAGGTGT
TGAGGTAGGTCGTGGTCAGCCATTAGGTGTGGGCATTAGTGGCCATCCTTTATTAAATAAATTGGATGAC
ACAGAAAATGCTAGTGCTTATGCAGCAAATGCAGGTGTGGATAATAGAGAATGTATATCTATGGATTACA
AACAAACACAATTGTGTTTAATTGGTTGCAAACCACCTATAGGGGAACACTGGGGCAAAGGATCCCCATG
TACCAATGTTGCAGTAAATCCAGGTGATTGTCCACCATTAGAGTTAATAAACACAGTTATTCAGGATGGT
GATATGGTTCATACTGGCTTTGGTGCTATGGACTTTACTACATTACAGGCTAACAAAAGTGAAGTTCCAC
TGGATATTTGTACATCTATTTGCAAATATCCAGATTATATTAAAATGGTGTCAGAACCATATGGCGACAG
CTTATTTTTTATTTACGAAGGGAACAAATGTTTGTTAGACATTTATTTAATAGGGCTGGTACTGTTGGT
GAAAATGTACCAGACGATTTATACATTAAAGGC▓▓▓▓▓▓▓▓▓▓▓▓▓▓▓▓▓▓▓▓▓▓▓▓▓▓▓▓▓▓▓▓▓CAAATTATT
TTCCTACACCTAGTGGTTCTATGGTTACCTCTGATGCCCAAATATTCAATAAACCTTATTGGTTACAACG
AGCACAGGGCCACAATAATGGCATTTGTTGGGGTAACCAACTATTTGTTACTGTTGTTGATACTACACGC
AGTACAAATATGTCATTATGTGCTGCCATATCTACTTCAGAAACTACATATAAAAATACTAACTTTAAGG
```

FIG. 10B

```
AGTACCTACGACATGGGGAGGAATATGATTTACAGTTTATTTTTCAACTGTGCAAAATAACCTTAACTGC
AGACGTTATGACATACATACATTCTATGAATTCCACTATTTTGGAGGACTGGAATTTTGGTCTACAACCT
CCCCCAGGAGGCACACTAGAAGATACTTATAGGTTTGTAACCCAGGCAATTGCTTGTCAAAAACATACAC
CTCCAGCACCTAAAGAAGATGATCCCCTTAAAAAATACACTTTTTGGGAAGTAAATTTAAAGGAAAAGTT
TTCTGCAGACCTAGATCAGTTTCCTTTAGGACGCAAATTTTTACTACAAGCAGGATTGAAGGCCAAACCA
AAATTTACATTAGGAAAACGAAAAGCTACACCCACCACCTCATCTACCTCTACAACTGCTAAACGCAAAA
AACGTAAGCTGTAAGTATTGTATGTATGTTGAATTAGTGTTGTTTGTTGTGTATATGTTTGTATGTGCTT
GTATGTGCTTGTAAATATTAAGTTGTATGTGTGTTTGTATGTATGGTATAATAAACACGTGTGTATGTGT
TTTTAAATGCTTGTGTAACTATTGTGTCATGCAACATAAATAAACTTATTGTTTCAACACCTACTAATTG
TGTTGTGGTTATTCATTGTATATAAACTATATTTGCTACATCCTGTTTTTGTTTATATATACTATATTT
TGTAGCGCCAGGCCCATTTTGTAGCTTCAACCGAATTCGGTTGCATGCTTTTTGGCACAAAATGTGTTTT
TTTAAATAGTTCTATGTCAGCAACTATGGTTTAAACTTGTACGTTTCCTGCTTGCCATGCGTGCCAAATC
CCTGTTTTCCTGACCTGCACTGCTTGCCAACCATTCCATTGTTTTTTACACTGCACTATGTGCAACTACT
GAATCACTATGTACATTGTGTCATATAAAATAAATCACTATGCGCCAACGCCTTACATACCGCTGTTAGG
CACATATTTTGGCTTGTTTTAACTAACCTAATTGCATATTTGGCATAAGGTTTAAACTTCTAAGGCCAA
CTAAATGTCACCCTAGTTCATACATGAACTGTGTAAAGGTTAGTCATACATTGTTCATTTGTAAAACTGC
ACATGGGTGTGTGCAAACCGATTTTGGGTTACACATTTACAAGCAACTTATATAATAATACTAA
```

FIG. 10C

```
ATTAATACTTTTAACAATTGTAGTATATAAAAAAGGGAGTAACCGAAAACGGTCGGGACCGAAAACGGTG
TATATAAAAGATGTGAGAAACACACCACAATACTATGGCGCGCTTTGAGGATCCAACACGGCGACCCTAC
AAGCTACCTGATCTGTGCACGGAACTGAACACTTCACTGCAAGACATAGAAATAACCTGTGTATATTGCA
AGACAGTATTGGAACTTACAGAGGTATTTGAATTTGCATTTAAAGATTTATTTGTGGTGTATAGAGACAG
TATACCCCATGCTGCATGCCATAAATGTATAGATTTTTATTCTAGAATTAGAGAATTAAGACATTATTCA
GACTCTGTGTATGGAGACACATTGGAAAAACTAACTAACACTGGGTTATACAATTTATTAATAAGGTGCC
TGCGGTGCCAGAAACCGTTGAATCCAGCAGAAAAACTTAGACACCTTAATGAAAAACGACGATTTCACAA
CATAGCTGGGCACTATAGAGGCCAGTGCCATTCGTGCTGCAACCGAGCACGACAGGAACGACTCCAACGA
CGCAGAGAAACACAAGTATAATATTAAGTATGCATGGACCTAAGGCAACATTGCAAGACATTGTATTGCA
TTTAGAGCCCCAAAATGAAATTCCGGTTGACCTTCTATGTCACGAGCAATTAAGCGACTCAGAGGAAGAA
AACGATGAAATAGATGGAGTTAATCATCAACATTTACCAGCCCGACGAGCCGAACCACAACGTCACACAA
TGTTGTGTATGTGTTGTAAGTGTGAAGCCAGAATTGAGCTAGTAGTAGAAAGCTCAGCAGACGACCTTCG
AGCATTCCAGCAGCTGTTTCTGAACACCCTGTCCTTTGTGTGTCCGTGGTGTGCATCCCAGCAGTAAGCA
ACAATGGCTGATCCAGAAGGTACAGACGGGGAGGGCACGGGTTGTAACGGCTGGTTTATGTACAAGCTA
TTGTAGACAAAAAAACAGGAGATGTAATATCAGATGACGAGGACGAAAATGCAACAGACACAGGGTCGGA
TATGGTAGATTTTATTGATACACAAGGAACATTTTGTGAACAGGCAGAGCTAGAGACAGCACAGGCATTG
TTCCATGCGCAGGAGGTCCACAATGATGCACAAGTGTTGCATGTTTAAAACGAAAGTTTGCAGGAGGCA
GCACAGAAAACAGTCCATTAGGGGAGCGGCTGGAGGTGGATACAGAGTTAAGTCCACGGTTACAAGAAAT
ATCTTTAAATAGTGGGCAGAAAAAGGCAAAAGGCGGCTGTTTACAATATCAGATAGTGGCTATGGCTGT
TCTGAAGTGGAAGCAACACAGATTCAGGTAACTACAAATGGCGAACATGGCGGCAATGTATGTAGTGGCG
GCAGTACGGAGGCTATAGACAACGGGGGCACAGAGGGCAACAACAGCAGTGTAGACGGTACAAGTGACAA
TAGCAATATAGAAAATGTAAATCCACAATGTACCATAGCACAATTAAAAGACTTGTTAAAAGTAAACAAT
AAACAAGGAGCTATGTTAGCAGTATTTAAAGACACATATGGGCTATCATTTACAGATTTAGTTAGAAATT
TTAAAAGTGATAAAACCACGTGTACAGATTGGGTTACAGCTATATTTGGAGTAAACCCAACAATAGCAGA
```

FIG. 11A

```
AGGATTTAAAACACTAATACAGCCATTTATATTATATGCCCATATTCAATGTCTAGACTGTAAATGGGGA
GTATTAATATTAGCCCTGTTGCGTTACAAATGTGGTAAGAGTAGACTAACAGTTGCTAAAGGTTTAAGTA
CGTTGTTACACGTACCTGAAACTTGTATGTTAATTCAACCACCAAAATTGCGAAGTAGTGTTGCAGCACT
ATATTGGTATAGAACAGGAATATCAAATATTAGTGAAGTAATGGGAGACACACCTGAGTGGATACAAAGA
CTTACTATTATACAACATGGAATAGATGATAGCAATTTTGATTTGTCAGAAATGGTACAATGGGCATTTG
ATAATGAGCTGACAGATGAAAGCGATATGGCATTTGAATATGCCTTATTAGCAGACAGCAACAGCAATGC
AGCTGCCTTTTTAAAAAGCAATTGCCAAGCTAAATATTTAAAAGATTGTGCCACAATGTGCAAACATTAT
AGGCGAGCCCAAAAACGACAAATGAATATGTCACAGTGGATACGATTTAGATGTTCAAAAATAGATGAAG
GGGGAGATTGGAGACCAATAGTGCAATTCCTGCGATACCAACAAATAGAGTTTATAACATTTTTAGGAGC
CTTAAAATCATTTTTAAAAGGAACCCCCAAAAAAAATTGTTTAGTATTTTGTGGACCAGCAAATACAGGA
AAATCATATTTTGGAATGAGTTTTATACACTTTATACAAGGAGCAGTAATATCATTTGTGAATTCCACTA
GTCATTTTTGGTTGGAACCGTTAACAGATACTAAGGTGGCCATGTTAGATGATGCAACGACCACGTGTTG
GACATACTTTGATACCTATATGAGAAATGCGTTAGATGGCAATCCAATAAGTATTGATAGAAAGCACAAA
CCATTAATACAACTAAAATGTCCTCCAATACTACTAACCACAAATATACATCCAGCAAAGGATAATAGAT
GGCCATATTTAGAAAGTAGAATAACAGTATTTGAATTTCCAAATGCATTTCCATTTGATAAAAATGGCAA
TCCAGTATATGAAATAAATGACAAAAATTGGAAATGTTTTTTGAAAGGACATGGTCCAGATTAGATTTG
CACGAGGAAGAGGAAGATGCAGACACCGAAGGAAACCCTTTCGGAACGTTTAAGTTGCGTGCAGGACAAA
ATCATAGACCACTATGAAAATGACAGTAAAGACATAGACAGCCAAATACAGTATTGGCAACTAATACGTT
GGGAAAATGCAATATTCTTTGCAGCAAGGGAACATGGCATACAGACATTAAACCACCAGGTGGTGCCAGC
CTATAACATTTCAAAAGTAAAGCACATAAAGCTATTGAACTGCAAATGGCCCTACAAGGCCTTGCACAA
AGTCGATACAAAACCGAGGATTGGACACTGCAAGACACATGCGAGGAACTATGGAATACAGAACCTACTC
ACTGCTTTAAAAAAGGTGGCCAAACAGTACAAGTATATTTTGATGGCAACAAAGACAATTGTATGACCTA
TGTAGCATGGGACAGTGTGTATTATATGACTGATGCAGGAACATGGGACAAAACCGCTACCTGTGTAAGT
CACAGGGGATTGTATTATGTAAAGGAAGGGTACAACACGTTTTATATAGAATTTAAAAGTGAATGTGAAA
AATATGGGAACACAGGTACGTGGGAAGTACATTTTGGGAATAATGTAATTGATTGTAATGACTCTATGTG
CAGTACCAGTGACGACACGGTATCCGCTACTCAGCTTGTTAAACAGCTACAGCACACCCCTCACCGTAT
TCCAGCACCGTGTCCGTGGGCACCGCAAAGACCTACGGCCAGACGTCGGCTGCTACACGACCTGGACACT
GTGGACTCGCGGAGAAGCAGCATTGTGGACCTGTCAACCCACTTCTCGGTGCAGCTACACCTACAGGCAA
CAACAAAAGACGGAAACTCTGTAGTGGTAACACTACGCCTATAATACATTTAAAAGGTGACAGAAACAGT
TTAAAATGTTTACGGTACAGATTGCGAAAACATAGCGACCACTATAGAGATATATCATCCACCTGGCATT
GGACAGGTGCAGGCAATGAAAAAACAGGAATACTGACTGTAACATACCATAGTGAAACACAAAGAACAAA
ATTTTTAAATACTGTTGCAATTCCAGATAGTGTACAAATATTGGTGGGATACATGACAATGTAATACATA
TGCTGTAGTACCAATATGTTATCACTTATTTTTTATTTTGCTTTTGTGTATGCATGTATGTGTGCTGCC
ATGTCCCGCTTTTGCCATCTGTCTGTATGTGTGCGTATGCATGGGTATTGGTATTTGTGTATATTGTGGT
AATAACGTCCCCTGCCACAGCATTCACAGTATATGTATTTTGTTTTTATTGCCCATGTTACTATTGCAT
ATACATGCTATATTGTCTTTACAGTAATTGTATAGGTTGTTTATACAGTGTATTGTACATTGTATATTT
TGTTTTATACCTTTTATGCTTTTTGTATTTTTGTAATAAAAGTATGGTATCCCACCGTGCCGCACGACGC
AAACGGGCTTCGGTAACTGACTTATATAAAACATGTAAACAATCTGGTACATGTCCACCTGATGTTGTTC
CTAAGGTGGAGGGCACCACGTTAGCAGATAAAATATTGCAATGGTCAAGCCTTGGTATATTTTGGGTGG
ACTTGGCATAGGTACTGGCAGTGGTACAGGGGGTCGTACAGGGTACATTCCATTGGGTGGGCGTTCCAAT
ACAGTGGTGGATGTTGGTCCTACACGTCCCCCAGTGGTTATTGAACCTGTGGGCCCCACAGACCCATCTA
TTGTTACATTAATAGAGGACTCCAGTGTGGTTACATCAGGTGCACCTAGGCCTACGTTTACTGGCACGTC
TGGGTTTGATATAACATCTGCGGGTACAACTACACCTGCGGTTTTGGATATCACACCTTCGTCTACCTCT
GTGTCTATTTCCACAACCAATTTTACCAATCCTGCATTTTCTGATCCGTCCATTATTGAAGTTCCACAAA
CTGGGGAGGTGGCAGGTAATGTATTTGTTGGTACCCCTACATCTGGAACACATGGGTATGAGGAAATACC
TTTACAAACATTTGCTTCTTCTGGTACGGGGAGGAACCCATTAGTAGTACCCCATTGCCTACTGTGCGG
CGTGTAGCAGGTCCCCGCCTTTACAGTAGGGCCTACCAACAAGTGTCAGTGGCTAACCCTGAGTTTCTTA
CACGTCCATCCTCTTTAATTACATATGACAACCCGGCCTTTGAGCCTGTGGACACTACATTAACATTTGA
TCCTCGTAGTGATGTTCCTGATTCAGATTTTATGGATATTATCCGTCTACATAGGCCTGCTTTAACATCC
```

FIG. 11B

```
AGGCGTGGGACTGTTCGCTTTAGTAGATTAGGTCAACGGGCAACTATGTTTACCCGCAGCGGTACACAAA
TAGGTGCTAGGGTTCACTTTTATCATGATATAAGTCCTATTGCACCTTCCCCAGAATATATTGAACTGCA
GCCTTTAGTATCTGCCACGGAGGACAATGACTTGTTTGATATATATGCAGATGACATGGACCCTGCAGTG
CCTGTACCATCGCGTTCTACTACCTCCTTTGCATTTTTAAATATTCGCCCACTATATCTTCTGCCTCTT
CCTATAGTAATGTAACGGTCCCTTTAACCTCCTCTTGGGATGTGCCTGTATACACGGGTCCTGATATTAC
ATTACCATCTACTACCTCTGTATGGCCCATTGTATCACCCACGGCCCCTGCCTCTACACAGTATATTGGT
ATACATGGTACACATTATTATTTGTGGCCATTATATTATTTTATTCCTAAGAAACGTAAACGTGTTCCCT
ATTTTTTTGCAGATGGCTTTGTGGCGGCCTAGTGACAATACCGTATATCTTCCACCTCCTTCTGTGGCAA
GAGTTGTAAATACCGATGATTATGTGACTCCCACAAGCATATTTTATCATGCTGGCAGCTCTAGATTATT
AACTGTTGGTAATCCATATTTTAGGGTTCCTGCAGGTGGTGGCAATAAGCAGGATATTCCTAAGGTTTCT
GCATACCAATATAGAGTATTTAGGGTGCAGTTACCTGACCCAAATAAATTTGGTTTACCTGATACTAGTA
TTTATAATCCTGAAACACAACGTTTAGTGTGGGCCTGTGCTGGAGTGGAAATTGGCCGTGGTCAGCCTTT
AGGTGTTGGCCTTAGTGGGCATCCATTTTATAATAAATTAGATGACACTGAAAGTTCCCATGCCGCCACG
TCTAATGTTTCTGAGGACGTTAGGGACAATGTGTCTGTAGATTATAAGCAGACACAGTTATGTATTTTGG
GCTGTGCCCCTGCTATTGGGGAACACTGGGCTAAAGGCACTGCTTGTAAATCGCGTCCTTTATCACAGGG
CGATTGCCCCCCTTTAGAACTTAAAAACACAGTTTTGGAAGATGGTGATATGGTAGATACTGGATATGGT
GCCATGGACTTTAGTACATTGCAAGATACTAAATGTGAGGTACCATTGGATATTTGTCAGTCTATTTGTA
AATATCCTGATTATTTACAAATGTCTGCAGATCCTTATGGGGATTCCATGTTTTTTGCTTACGGCGTGA
GCAGCTTTTTGCTAGGCATTTTTGGAATAGAGCAGGTACTATGGGTGACACTGTGCCTCAATCCTTATAT
ATTAAAGGCACAGGTATGCCTGCTTCACCTGGCAGCTGTGTGTATTCTCCCTCTCCAAGTGGCTCTATTG
TTACCTCTGACTCCCAGTTGTTTAATAAACCATATTGGTTACATAAGGCACAGGGTCATAACAATGGTGT
TTGCTGGCATAATCAATTATTTGTTACTGTGGTAGATACCACTCCCAGTACCAATTTAACAATATGTGCT
TCTACACAGTCTCCTGTACCTGGGCAATATGATGCTACCAAATTTAAGCAGTATAGCAGACATGTTGAGG
AATATGATTTGCAGTTTATTTTTCAGTTGTGTACTATTACTTTAACTGCAGATGTTATGTCCTATATTCA
TAGTATGAATAGCAGTATTTTAGAGGATTGGAACTTTGGTGTTCCCCCCCCCCAACTACTAGTTTGGTG
GATACATATCGTTTTGTACAATCTGTTGCTATTACCTGTCAAAAGGATGCTGCACCGGCTGAAAATAAGG
ATCCCTATGATAAGTTAAAGTTTTGGAATGTGGATTTAAAGGAAAAGTTTTCTTTAGACTTAGATCAATA
TCCCCTTGGACGTAAATTTTGGTTCAGGCTGGATTGCGTCGCAAGCCCACCATAGGCCCTCGCAAACGT
TCTGCTCCATCTGCCACTACGTCTTCTAAACCTGCCAAGCGTGTGCGTGTACGTGCCAGGAAGTAATATG
TGTGTGTGTATATATATACATCTATTGTTGTGTTTGTATGTCCTGTGTTTGTGTTTGTTGTATGATTG
CATTGTATGGTATGTATGGTTGTTGTTGTATGTTGTATGTTACTATATTGTTGGTATGTGGCATTAAAT
AAAATATGTTTTGTGGTTCTGTGTGTTATGTGGTTGCGCCCTAGTGAGTAACAACTGTATTTGTGTTTGT
GGTATGGGTGTTGCTTGTTGGGCTATATATTGTCCTGTATTTCAAGTTATAAAACTGCACACCTTACAGC
ATCCATTTTATCCTACAATCCTCCATTTTGCTGTGCAACCGATTTCGGTTGCCTTTGGCTTATGTCTGTG
GTTTTCTGCACAATACAGTACGCTGGCACTATTGCAAACTTTAATCTTTTGGGCACTGCTCCTACATATT
TTGAACAATTGGCGCGCCTCTTTGGCGCATATAAGGCGCACCTGGTATTAGTCATTTTCCTGTCCAGGTG
CGCTACAACAATTGCTTGCATAACTATATCCACTCCCTAAGTAATAAAACTGCTTTTAGGCACATATTTT
AGTTTGTTTTTACTTAAGCTAATTGCATACTTGGCTTGTACAACTACTTTCATGTCCAACATTCTGTCTA
CCCTTAACATGAACTATAATATGACTAAGCTGTGCATACATAGTTTATGCAACCGAAATAGGTTGGGCAG
CACATACTATACTTTTC
```

DENDRON-MEDIATED DNA VIRUS DETECTION

RELATED APPLICATIONS

This application is a continuation-in-part of U.S. patent application Ser. No. 11/616,761, filed Dec. 27, 2006, which claims priority from U.S. Provisional Patent Application 60/755,503, filed Dec. 29, 2005, both of which are hereby incorporated by reference as if fully set forth.

FIELD OF THE DISCLOSURE

This disclosure relates to chips containing nucleic acid probes or primers and their use in methods to detect nucleic acid molecules. The disclosure also provides DNA chips and their use in the detection of gene sequences in one step.

BACKGROUND OF THE DISCLOSURE

In general, the microarrays of single-stranded oligonucleotides (usually DNA or PNA) immobilized on the surface of glass or other solid surfaces are used for various purposes: identification or detection of infectious agents such as virus, bacteria, and other forms of microorganism, genotyping, disease causing genes, mutation of genes, expression of genes, etc. In some instances, the technology has also been adapted for diagnosis at hospitals and clinics. In other instances, various technologies have been consolidated and optimized for convenient use and or reliable decisions in connection with clinical diagnosis.

The use of DNA chip often requires long processes such as (a) extraction of DNA or RNA from biological specimens such as tissues, cells, blood, serum, and biological fluids, (b) amplification of target regions of genes by polymerase chain reaction (PCR), or conversion of RNA to cDNA and subsequent amplification of cDNA, (c) labeling of amplified DNA with fluorescent tags, often during PCR, (d) hybridization of the amplified DNA with the oligonucleotides (often called capture probes) immobilized on the surface of a solid substrate such as glass, and (e) scanning of the slide in a detector such as a laser scanner.

With respect to extraction, DNA or RNA is obtained from biological specimens by well established protocols (Molecular Cloning: A laboratory manual by Sambrook and Russel, $3^{rd}$ Edition, Cold Spring Harbor Laboratory Press, 2001). Typically cells are lysed in a buffer containing SDS and proteinase K for degradation of proteins, the lysate is extracted with phenol/chloroform, and the DNA or RNA in the phenol layer is precipitated with ethanol.

Several companies have introduced more simplified protocols for high throughput purification of DNA and RNA from biological specimens. In general, these procedures take advantage of the binding property of DNA and RNA to silica powder, silica fiber or silica membrane (GE Heatlth, Qiagen, etc.). These procedures, although can be accomplished in 30 minutes to one hour, requires multiple pipetting, and many manipulations.

As an example, one protocol is briefly described. Biological specimens such as cells are suspended in 200 μl PBS (phosphate buffered saline) and centrifuged (300 g for 5 min). To the pelleted cells 200 μl lysis buffer and 20 μl proteinase K is added. The mixture is incubated at 70° C. for 10 min. Ethanol (200 μl) is added and the tube is vortexed. The lysed cells are transferred into the Mini spin column (with a silica membrane bottom) placed into a 2 ml collection tube and centrifuged at 6000×g for 1 minute and the collection tube is discarded. The Mini-spin column is transferred to another collection tube, 500 μl of wash buffer is added to the Mini spin column and centrifuged. The collection tube is discarded and the Mini-spin column is transferred to another collection tube. A second wash buffer (500 μl) is added and the tube is centrifuged. The Minispin column is transferred to another collection tube, and 200 μl of elution buffer is added to the mini-spin column followed by centrifugation. The collection tube is saved. The Minispin column is then transferred to another collection tube and second elution buffer is added to the Mini-spin column and centrifuged again. The collection tube is saved. The DNA in two collection tubes are combined. As seen from this example, extraction of DNA from cells requires about 10 pipetting steps and several centrifugation steps and many manipulations such as transfer of Mini-spin column to different collection tubes, etc. Purification of RNA also requires a similar process.

Similar protocols are adopted for extraction of nucleic acids from multiple samples in an automated format.

Often, the target DNA or RNA sequences for diagnosis are present in biological samples in a very minute amount, and there is need for amplification of target DNA or RNA sequences before nucleic acid diagnosis. One method for amplification of target DNA sequences is polymerase chain reaction (PCR). Generally, the PCR process involves denaturation of DNA (strand separation) at a high temperature (95° C.), annealing of short primers (usually 15-20 nucleotides) that are complementary to either ends of a DNA region to be amplified, and chain elongation from the annealed primers in the presence of thermostable DNA polymerase and four deoxynucleotide triphosphates. These processes require specific temperatures: for example, 90° C. or above for denaturation, 55-65° C. for annealing, and 72° C. for chain elongation. Denaturation, annealing and chain elongation are repeated continuously until desired amount of DNA is amplified, typically 20-30 cycles. Therefore, PCR requires a programmable thermocycler.

For amplification of a RNA sequence, the RNA is first converted to double-stranded cDNA in the presence of reverse transcriptase and DNA polymerase, DNA primers and four deoxynucleotide triphosphates. Subsequently, cDNA is amplified by PCR as described above. The process of cDNA synthesis and subsequent PCR may be carried out in one reaction mixture.

After PCR or cDNA synthesis and subsequent PCR, the amplified product is purified to remove the remaining primers and deoxynucleotide triphosphates. The PCR products are often identified by gel electrophoresis and staining of the amplified DNA with ethidium bromide or CYBR GREEN® dye. [spelled Sybr Green in claim 8]

For use of the amplified DNA in diagnosis by DNA chip, the amplified DNA is labeled. For example, a fluorescently labeled deoxynucleotide (Cy3 or Cy5-deoxy nucleotide triphosphate, ALEXA FLUOR®-deoxynucleotide triphosphate) is added to PCR reaction mixture. PCR primers that are labeled with fluorescent group or biotin can also be used for labeling amplified DNA. The biotin-labeled DNA can be detected by interaction with labeled streptavidin. The fluorescently labeled DNA can be detected by laser scanner.

After PCR, the labeled PCR product is purified by use of various protocols. One of which can be the protocol described above by use of silica membrane for extraction of DNA from cells and tissues.

The labeled PCR product is added to hybridization buffer. The mixture is heated to 95° C. to convert the labeled amplified DNA to single-stranded form and quickly chilled on ice and transferred on to a chamber assembled on the surface of a chip slide (usually a glass slide) that has immobilized single-stranded oligonucleotide (15-70 nucleotides) capture probes. The slide is then incubated at a temperature for annealing (such as from 40-65° C.). After hybridization, the chamber is disassembled and the slide is washed once with 1×SSC+0.1% SDS, once with 0.1×SSC+0.1% SDS and once with 1×SSC, all as non-limiting examples.

A DNA chip is typically a slide on which capture probes (short single-stranded DNA) are immobilized in a high density format. In many cases, a glass slide is coated with chemicals to attach the capture probes to the glass. The chemicals should not only attach the DNA to the glass surface but also minimize non-specific binding and signal noise. For example, the chemicals on a chip slide contain silanated, silylated, or poly-L-lysine as a source of an amine or an aldehyde group for attachment of DNA. Recently, dendrons have been developed for use in a biochip. When a chip is coated with dendrons, one can control spacing between capture probes and this also allows reduction of steric hinderance and concomitant increase in sensitivity. Korean patent 10-0383080-0000, and published U.S. Patent Application 2005/0037413 describe dendrons that provide controlled spacing as well as density of amines on dendron.

Single-stranded oligonucleotides whose length can vary from 15 to 70 nucleotides are often used as capture probes that will hybridize to the complementary strand sequences of target genes, DNA or RNA. PNA may also be used as capture probes. The oligonucleotides will have either amine or SH group at 3' or 5' ends, usually at 3' end so that the oligonucleotides can be crosslinked to the surface of chip slide.

When DNA chip slides are used, the sequence of steps is to amplify the DNA (labeling the DNA with fluorescent group at the same time) and then purify the DNA. The amplified DNA is denatured by heating and added to the surface of capture probes for annealing. After hybridization, the slide is washed and the fluorescent double-stranded DNA is detected by scanning and the data are analyzed.

As evident from above, the whole process from extraction of nucleic acids, gene amplification, and subsequent hybridization of the amplified DNA with the capture probes on chip slide requires multiple processes such as many repeated transfer (pipetting), mixing of solutions, centrifugations, etc. Even when automated machine is developed for extraction of DNA and RNA, there is still need for coupling of this technology with PCR and hybridization with capture probes on chip surface.

Additionally, there is a requirement for considerable time for gene amplification and purification (as much as one day). Also, the cost of chemicals and disposable items is high. There is also loss of sample during purification of reaction products. Therefore, there is need for streamlining the cumbersome processes involved in use of gene chips to reduce losses and variation of the results.

There have been attempt to carry out PCR in a single step from biological specimens. For example, cells are directly added to PCR reaction mixture. Several companies have introduced one-step PCR mixtures that allow amplification of DNA from whole cells or blood. These mixtures contain detergent to facilitate lysis of cells, proteinase K for digestion of proteins, and often proprietary agents. The efficiency of PCR is variable.

Reverse transcription of RNA to synthesize cDNA with subsequent PCR can also be carried out in one step with whole cells. However, the efficiency again varies depending on the type of biological specimens. For example, blood and serum contains inhibitor of reverse transcriptase.

There have also been attempts to couple DNA and RNA extraction by an automated process and PCR. Several companies introduced combined procedures for automated extraction of DNA or RNA and automated PCR. Although these automated processes satisfy diagnosis of certain diseases as well as quantitation of target nucleic acid sequences, such as those of infectious biological agents, it is difficult to use PCR for identification of different variants of a virus (genotypes), changes in sequences in response to drug-resistance, and the mutations of target genes that cause diseases.

A DNA chip offers many advantages over diagnosis by PCR or by immunologic assays. With a DNA chip, it is possible to identify, all at once, many different sequences, changes of sequences by mutation, different genotypes of viruses, and expression of different genes. However, there is clear need for simplification and integration of all necessary protocols for extraction of nucleic acids, gene amplification and hybridization on chip surface in order for the DNA chip technology to be used at hospitals and clinics with increased throughput and reduction in manual labor. Current technology requires highly trained technicians, long processes, high cost and time. Even when automated systems are available, it requires at least three different systems, such as automated extraction of nucleic acids, gene amplification, and hybridization on DNA chip.

There is also an increasing need for diagnosis of disease-causing agents such as viruses and the changes in gene sequences that cause formation of tumors for personalized drug therapy or vaccination. For example, GLEEVEC® (imatinib) is highly effective for treatment of some cases of chronic myeloid leukaemia (CML) and also gastrointestinal stromal tumour (GIST). Gleevec specifically blocks ATP-binding sites on specific mutant tyrosine kinases in the responsive cancers. Therefore, it is necessary to detect the mutant tyrosine kinase genes before treatment of the cancer. Similarly, various oncogenic DNA and RNA viruses are known to induce tumor formation in humans. Prevention of these cancers, such as cervical cancer, requires early detection and treatment of pre-cancerous disease.

Papiloma viruses are a diverse group of DNA-based viruses that infect the skin and mucous membranes of humans and a variety of animals. Over 100 different human papilloma virus (HPV) types have been identified. Some HPV types may cause warts while others may cause a subclinical infection resulting in precancerous lesions. All HPVs are transmitted by skin-to-skin contact.

A group of about 30-40 HPVs is typically transmitted through sexual contact and infect the anogenital region. Some sexually transmitted HPVs (types 6 and 11) may cause genital warts.

Persistent infection with a subset of about 13 so-called "high risk" sexually transmitted HPVs, including types 16, 18, 31, 33, 35, 39, 45, 51, 52, 56, 58, 59, and 68 (different from the ones that cause warts) may lead to the development of cervical intraepithelial neoplasis (CIN), vulvar intraepithelial neoplasia (VIN), penile intraepithelial neoplasia (PIN), and/or anal intraepithelial neoplasia (AIN). These are precancerous lesions that can progress to invasive cancer. HPV infection is a necessary factor in the development of nearly all cervical cancer (Walboomers, J M, Jacobs M V, Manos M M et al (1999) "Human papillomavirus is a necessary cause of invasive cervical cancer worldwide" J. Pathol. 189:12-9).

According to the Center for Disease Control (CDC), by the age of 50 more than 80% of the American women will have contracted at least one strain of genital HPV. All women are encouraged to get a yearly pap smear solely to detect cellular abnormalities caused by HPV. About 14,000 women in the United States are diagnosed with cervical cancer disease each year, and more than 3,900 women die in the United States each year from this disease.

Among the high risk HPV strains, type 16 and 18 are together responsible for over 65% of cervical cancer cases.

An HPV test detects certain types of HPVs, depending of the test. A method for detecting the DNA of high-risk HPVs has recently been added to the range of clinical options for cervical cancer screening. In March 2003, the US FDA approved a "hybrid-capture" test (see U.S. Pat. No. 6,228,578 B1), marketed by Digene, as a primary screening tool for detecting high-risk HPV infections that may lead to cervical cancer. This test was also approved for use as an adjunct to Pap testing, and may be ordered in response to abnormal Pap smear results.

The principle of Digene test is briefly summarized as follows. An exfoliated cervical cell sample is collected in a collection device and nucleic acids are released therefrom. A diluent containing multiple RNA probes to different HPV types is added. The mixture is incubated to allow hybridization of the RNA probes to the HPV sequences. The mixture is then combined with an immobilized antibody for DNA-RNA duplex, and complexes allowed to form. RNase is then added to digest away non-hybridized probe RNA. Labeled monoclonal anti-hybrid antibody is added to the tube. After incubation, excess RNase and conjugate is discarded and the hybrids detected.

The Digene test has some advantages: simplicity, rapidity, and quantitation of HPV. One major drawback of the Digene test appears to be difficulty of identification of the HPV type since mixtures of RNA probes for different HPV types are used. This is significant in view of the fact that there are many types of cancer-causing HPV types and current HPV vaccine will not protect humans from all types of HPV that cause cervical cancer. Therefore, the test is inadequate for complete identification of HPV type (s) in the infected cervical cells.

On Jun. 8, 2006, the FDA approved GARDASIL®, a prophylactic HPV vaccine which is marketed by Merck. The vaccine shows protection against initial infection with HPV types 16 and 18. Since the current vaccine will not protect women against all the HPV types that cause cervical cancer, it will be important for women to continue to seek Pap smear testing and other types of testing even after receiving the vaccine.

Various methods are available for identification of HPV type (genotyping). For example, a labeled HPV type-specific probe (labeled with radioisotope, fluorescence, biotin, etc) is directly hybridized with cellular DNA (usually after extraction and purification) in several formats. Liquid hybridization (such as the Digene "hybrid capture"), Southern and dot blot hybridization, and fluorescent in situ hybridization (FISH) are non-limiting examples. Gene amplification methods are also used. For example, HPV DNA is amplified by PCR by use of type-specific primers. However, this method suffers from the difficulty of identification of different types of HPVs in one experiment. The amplified DNA (usually labeled during PCR) can be used for hybridization with type-specific capture probes in dot blot, microtiter plate hybridization, or line probe assay in a similar way as DNA chip. However, these methods lack sensitivity and suffer from difficulties in data interpretation. DNA chip offers possibility of identification of many different types of HPV at once.

Recently, Biomedlab (Seoul, Korea) has offered a DNA chip that has capture probes for as many as 30 different types of HPVs on a single chip that can distinguish low-risk as well as high-risk HPVs with high specificity and sensitivity (U.S. Pat. No. 7,301,015). The use of this chip requires purification of DNA from patient cervical cells, PCR and labeling of amplified HPV DNA, and hybridization of the amplified DNA with the type-specific capture probes immobilized on glass slide surface.

Citation of the documents herein is not intended as an admission that any is pertinent prior art. All statements as to the date or representation as to the contents of these documents is based on the information available to the applicant and does not constitute any admission as to the correctness of the dates or contents of these documents.

SUMMARY OF THE DISCLOSURE

This disclosure relates to methods for gene diagnosis or detection by DNA chip in one step. Put differently, the methods may be considered as integrating all steps needed for use of a DNA chip to detect nucleic acid molecules. The disclosure may be advantageously used to conduct DNA based diagnosis, via nucleic acid detection, in one chamber on a slide in an automatic or semi-automatic manner by simply changing the temperature and duration of a series of reactions using a temperature cycler.

In many embodiments, the disclosure may be applied to the detection or identification of all or part of a DNA molecule, such as that of a DNA virus like papillomavirus or hepadnavirus as non-limiting examples. In some cases, the detection or identification may be of a papillomavirus DNA sequence, including human papillomavirus (HPV) as a non-limiting example. In some embodiments, the detection or identification may be of a particular type or strain of papillomavirus, such as a particular HPV type or strain. In other cases, the detection or identification may be of a hepadnavirus. The detection or identification may be of a particular type or strain of hepadnavirus, such as hepatitis B virus (HBV) or a type or strain of HBV (such as types A, B, C, and D), as non-limiting examples.

Thus a simple process for diagnosis of a DNA virus, such as an HPV or HBV, by DNA chip is disclosed which does not require extraction of nucleic acids. After a simple treatment of cells, gene amplification from DNA and hybridization can be carried out on the surface of a DNA chip, all in one chamber without changing solution(s). This procedure can be applied to various cell containing samples, with cervical cells and blood-borne cells as non-limiting examples.

Where extraction of nucleic acids is required for diagnosis by DNA chip, gene amplification from DNA and hybridization can be carried out on the DNA chip surface, all in one chamber without changing solution.

The integrated process advantageously saves labor, time and cost and can be easily adopted for automation of DNA chip.

In a first aspect, the disclosure includes a DNA chip with a plurality of nucleic acid probes immobilized on a surface of the chip. The surface may be one facing an enclosed, interior space (or volume) on the chip. The enclosed volume may be a chamber with a removably attached side or other opening (which maybe closed) capable of containing a liquid reaction volume for preparing or manipulating nucleic acid molecules. In operation, the reaction volume contains a nucleic acid molecule to be detected, which molecule is amplified at least in part. The substance containing a nucleic acid molecule to be detected may be added directly to the reaction volume so that matter normally or commonly found with the nucleic acid molecule is also present in the reaction volume.

So in some cases, a biological sample containing, or suspected to contain, the nucleic acid to be detected is added to the reaction volume. The sample may contain a cell with the nucleic acid molecule to be detected. In some embodiments, the cell may be a cervical cell, such as that obtained from a human patient. In other embodiments, the sample may contain a cell extract or lysate or supernatant after removal of precipitated or other contaminating materials.

The reaction volume would also contain other reagents necessary for nucleic acid amplification. The amplification may be repetitive, such that multiple cycles of nucleic acid amplification occur to produce a detectable amount of amplified nucleic acid material. The amplified nucleic acid material is detected based upon its attachment to the chip via the immobilized probes. The attachment is via base pair interactions between the material and the immobilized probes. In some embodiments, the probes detect one or more papillomavirus sequences, such as one or more human papillomavirus (HPV) sequences as a non-limiting example. In other embodiments, the probes detect one or more hepadnavirus sequences, such as one or more HBV sequences. The interactions are facilitated by hybridization of the amplified material to the immobilized probes. After attachment of the amplified material, it is detected by a suitable means of scanning the chip and analyzing the presence or amount of attached amplified material. In the case of papillomavirus, with HPV and cervical cells as a non-limiting example, the disclosure provides for the diagnosis of HPV in a subject. In the case of a hepadnavirus, with HBV and blood borne cells as a non-limiting example, the disclosure provides for the diagnosis of HBV in a subject.

In many embodiments of the disclosure, detection of the amplified nucleic acids is aided by the use of one or more deoxynucleotide triphosphates attached to a detectable label. The triphosphates are incorporated into the amplified nucleic acid material by the polymerase used so that the amplified material contains the detectable label. The amplification of nucleic acid material, and so incorporation of the triphosphates, maybe advantageously performed by use of the Polymerase Chain Reaction (PCR). This also allows the methods of the disclosure to be practiced by use of a programmable thermocycler which cycles the reaction volume on the chip.

The incorporation of a detectable label facilitates detection of the amplified nucleic acid material when they are attached to the chip. To further facilitate detection, the chip may be washed or rinsed to remove or reduce the amount of non-attached material so that interference with the detection of the amplified material is reduced or minimized.

In another aspect, the disclosure includes a method for detecting a DNA virus nucleic acid molecule, such as that of a papillomavirus or hepadnavirus. In some embodiments, the molecule is in a sample, such as a biological sample as a non-limiting example. In some cases, the method includes amplifying a nucleic acid molecule of the DNA virus, such as that in a biological sample, by use of a pair of primers in a polymerase chain reaction (PCR). The amplifying results in the production of amplified material, or an amplicon, that contains a DNA virus (such as papillomavirus or hepadnavirus) nucleic acid sequence.

The amplifying may also be conducted in the presence of a single stranded nucleic acid probe, complementary to said amplified DNA virus (such as papillomavirus or hepadnavirus) molecule, immobilized via a dendron on a solid surface. The amplified material is then allowed to hybridize to the probe to form a double stranded complex, followed by detecting the complex. The detection of the complex may of course be used as an indication of the presence of the corresponding virus in the sample, and so in the subject (such as a human patient as a non-limiting example) from whom the sample was obtained.

In some embodiments, the papillomavirus is a human papillomavirus (HPV), such as one of the more than 100 HPV types that are associated with certain types of cancer (referred to as "high-risk" oncogenic or carcinogenic HPVs) or that may cause warts, or papillomas, which are benign (noncancerous) tumors. In some cases, the HPV is HPV type 16, HPV type 18, HPV type 31, HPV type 33, HPV type 35, HPV type 39, HPV type 45, HPV type 51, HPV type 52, HPV type 56, HPV type 58, HPV type 59, or HPV type 68.

As a further aspect, the method may be a multiplex format wherein more than one papillomavirus nucleic acid molecule is amplified and detected as disclosed herein. In some cases, the detection is by use of more than one probe, each of which detects a separate papillomavirus nucleic acid molecule as disclosed herein. In some cases, the more than one nucleic acid molecule is from more than one HPV, such as HPV type 16 and HPV type 18, or HPV type 53 and HPV type 58, as non-limiting examples.

In embodiments of the disclosure related to a hepadnavirus, the virus may be a strain or type of HBV, which may be considered the prototypical member of the family Hepadnaviridae, which includes Orthohepadnavirus and Avihepadnavirus which are DNA viruses within the scope of the instant disclosure. The disclosure further includes a multiplex method wherein more than one hepadnavirus DNA molecule, such as more than one HBV DNA molecule, is amplified and detected as described herein. In some cases, the more than one includes one or more mutant HBV molecules as known to the skilled person and/or described herein. The detection may be by use of more than one probe, each of which detects a separate hepadnavirus DNA molecule, such as a separate HBV DNA molecule. Additional embodiments include use of one or more probes that detect one or more mutant HBV DNA molecules.

As one non-limiting embodiment, a method of the disclosure for gene amplification and hybridization includes the following: (1) a slide; (2) the surface of the slide coated with dendron; (3) DNA capture probes attached on top of the dendron; (4) an incubation chamber created on the surface that contains the DNA capture probes; (5) direct addition of biological sample to a gene amplification reaction mixture in the chamber; (6) gene amplification and hybridization in the same incubation chamber on the slide; (7) scanning of the slide and analysis of the results. In other embodiments, the methods of the disclosure may be adapted for performance in a semi-automated or fully automated manner.

The methods of the disclosure save time and effort, and minimize errors that arise from other methods using many handling steps, such as those involved in the isolation of nucleic acids from biological samples and in the isolation of amplified DNA material, gene amplification and purification, transfer of amplified samples to hybridization mixture, and so forth.

The details of additional embodiments of the disclosure are set forth in the accompanying drawings and the description below. Other features and advantages of the disclosure will be apparent from the drawings and detailed description, and from the claims.

Definitions

As used herein, the terms annealing and hybridization mean the same process: duplex formation between two strands of single stranded nucleic acid molecules, such as DNA or PNA as non-limiting examples, by base complementarity. The term "detect" or a variant thereof includes both quantitative and qualitative methods of detection.

The term "DNA chip" refers to a solid support with one or more attached nucleic acid based probes capable of detecting a nucleic acid sequence, such as that of a DNA molecule. The probes may be in the form of DNA or PNA or other suitable molecular structure as known in the industry.

The term "DNA virus" refers to a virus which has a genome that is composed of deoxyribonucleic acid (DNA) as opposed to ribonucleic acid (RNA).

As used herein, "comprise" or "comprising" or "include" or "including" or variants thereof are used in the "open" sense such that the terms are inclusive and permit the presence of additional elements. The terms specify the presence of the stated features, steps, or components as recited without precluding the presence or addition of one or more features, steps, or components.

BRIEF DESCRIPTION OF THE DRAWINGS

FIG. 10A-10C show the complete genome sequence of a representative human papillomavirus type 16, which is also identified by the accession numbers GI 9627100 and NC_001526.1. The L1 gene (nucleotides 5559 to 7154) is underlined while the regions corresponding to non-limiting forward and reverse primers are boxed. The region corresponding to a representative capture probe is shaded.

FIG. 11A-11C show the complete genome sequence of a representative human papillomavirus type 18, which is also identified by the accession numbers GI 9626069 and NC_001357.1. The L1 gene (nucleotide 5430 to 7136) is underlined while the regions corresponding to non-limiting forward and reverse primers are boxed. The region corresponding to a representative capture probe is shaded.

DETAILED DESCRIPTION OF MODES OF PRACTICING THE INVENTION

General

The disclosure includes methods to simplify the amplification and detection of nucleic acid molecules. In some embodiments, the methods may be advantageously used in a "one step" process of detecting nucleic acid molecules in a biological sample with reduced handling and/or manipulation of the sample as well as the reactions used to amplify the nucleic acids.

Figure 1:
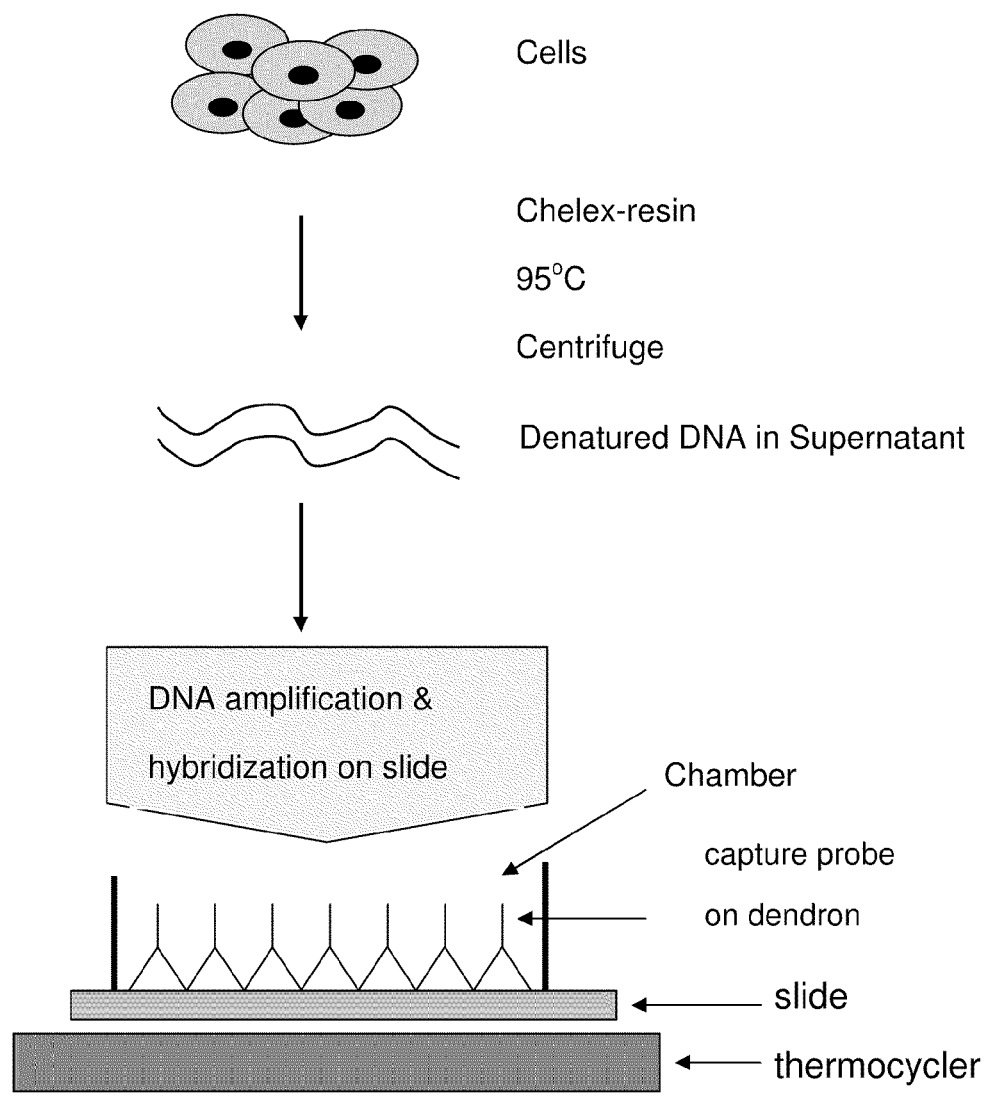
FIG. 1 illustrates the basic concept of the integrated process of diagnosis by DNA chip FIG. 2 demonstrates the validity of the capture probes for HPV 16 and HPV 18. The plasmids containing either HPV16 or HPV18 were amplified by PCR, and the PCR mixture was loaded on DNA chip and hybridized with the capture probes.

So a simple integrated process for diagnosis by DNA chip is described. This process can be easily adapted for a biological specimen from which cellular nucleic acid material can be recovered. As an example, an integrated process for diagnosis of different types of HPV from the infected cervical cells is provided. FIG. 1 illustrates a non-limiting example for the basic integrated process using a chip with capture probes, such as DNA or PNA probes as non-limiting examples.

A nucleic acid molecule to be amplified and detected according to the disclosed disclosure may be any that is of interest, such as genomic DNA of a cell, viral DNA of a DNA virus. Thus a nucleic acid molecule may be a gene, a part of a gene or genome (such as all or part of a coding region).

In some embodiments, the nucleic acid molecule is present in whole blood, one or more cells, or a virus or viral particle. The nucleic acid molecule may be amplified, such as by PCR as described herein, or used for synthesis of a cDNA molecule. The nucleic acid molecule, or the amplified or cDNA form thereof, may also be hybridized to a probe containing solid surface as described herein. In some cases, the nucleic acid molecule is a DNA molecule of a virus which is present in an infected cell or viral particle and detected as described herein. The detection may be used to diagnose an infection by the virus (or presence of an infected cell) and/or presence of the virus. The disclosed methods also make automation of gene diagnosis in hospitals and clinics possible. The disclosed methods save time and effort involved in nucleic acid DNA extraction from the cells and in purification of gene amplification products. The disclosed methods also minimize the loss of sample that occurs during the purification of gene amplification product thus increasing reproducibility and reliability of the diagnosis involving DNA chip.

Preparation of Sample or Specimen

Whole Cells or Tissues

In some embodiments, a sample such as an exfoliated cervical cell specimen as a non-limiting example, is collected and subjected to heating at 95° C. in the presence of 5% Chelex-100 resin (Bio-Rad Laboratories, Hercules, Calif., USA), or another styrene-divinylbenzene copolymer with attached imminodiacetate functional groups. Insoluble debris is removed, such as by centrifugation to product a supernatant containing cellular contents, including nucleic acid material. The supernatant may be directly used for gene amplification on DNA chip surface as described herein.

In alternative embodiments, whole cells can also be directly added to the PCR reaction mixture. The PCR reaction and hybridization may then be carried out on the surface of DNA chip.

Of course cells obtained from a cell-containing tissue sample may be used. In some cases, cells obtained from a tissue sample are prepared as described above and used in the disclosure.

In some embodiments, the cell-containing sample contains cells obtained by an abrasive technique, such as those obtained via a Pap test as a non-limiting example, or a biopsy, such as from the vagina or cervix.

Blood

In further embodiments, blood may be used for diagnosis as described herein. As in the case of cells, insoluble material that may be formed should be removed prior to PCR and hybridization on the surface of chip slide as described herein. In some cases, heating or microwave of a blood sample forms insoluble material, containing proteins and other materials which may be removed without significant affect on the practice of the disclosure. Optionally, the heating may be at a temperature such as that which is used during the PCR process. After removal of the insoluble material, the resulting supernatant contains denatured DNA which can be used for direct PCR and hybridization as disclosed herein.

In one non-limiting embodiment, whole blood is treated with red cell lysis buffer and the white blood cells are collected by low speed centrifugation. The white cells are heated at 95° C. in the presence of Chelex-resin or other similar copolymer. The resulting supernatant contains denatured DNA, RNA and other soluble proteins. To assay target DNA, the supernatant can be used directly for amplification as disclosed herein. The presence of RNA will not interfere with PCR due to the specific nature of the reaction.

Blood may be advantageously used in cases of "serum hepatitis" (HBV) or other hepadnavirus DNA as described herein.

Serum

In another embodiment, serum may be used as a DNA containing sample as disclosed herein. In some embodiments, the serum may contain a DNA virus, such as Hepatitis B virus. Similar to the case of a blood sample, insoluble material that may form during PCR and it should be removed prior to PCR and hybridization on the surface of chip slide as described herein. Additionally, the possible quenching of fluorescence may present a difficulty to be addressed by the selection of detectable signals that are less subject to quenching.

In some cases, heating of a serum sample forms insoluble material and may be used to remove proteinaceous material. The heating may be optionally at a temperature such as that which is used during the PCR process. After removal of the insoluble material, the resulting supernatant contains denatured DNA which can be used for direct PCR and hybridization as disclosed herein. In other embodiments, Chelex-resin, or other similar copolymer, is present during the heating step. Without being bound by theory, and offered to improve the understanding of the disclosure, it is believed that the presence of the resin (or other copolymer) results in less DNA degradation.

Alternatively, digestion of serum with proteinase K and heating with Chelex resin (or other similar copolymer) as described herein may be used.

Serum may be advantageously used in cases of HBV or other hepadnavirus DNA as described herein.

Direct PCR and Detection

In one aspect, the disclosure includes methods for the direct PCR of a biological sample. In some embodiments, the sample is a cell or tissue containing sample wherein a nucleic acid molecule to be detected is present in the cell or tissue. The sample may be added directly to a reaction (or incubation) chamber on a solid surface, such as on a slide or chip, of the disclosure and mixed with the reagents needed for amplifying the nucleic acid molecule to be detected. Non-limiting examples include embodiments wherein the solid surface is on a microarray or in a cell or chamber of a solid medium. After amplification, the amplified material is hybridized to probes immobilized on the solid surface, such as on a chip surface within a chamber, and detected. The detection may be qualitative in nature with respect to the presence or absence of a nucleic acid molecule in a sample. Alternatively, the detection may be quantitative in nature to determine the amount of a nucleic acid molecule in a sample.

In some embodiments, a method for detecting a nucleic acid molecule in a sample is provided. The method comprises amplification of the nucleic acid molecule in the presence of a single stranded nucleic acid probe complementary to the molecule where the probe is attached to a solid surface by a dendron. If the nucleic acid molecule is double-stranded, the probe is complementary to one strand of the molecule. The method may be used to amplify a nucleic acid molecule, in a sample, by use of two primers in a polymerase chain reaction (PCR) to produced amplified nucleic acid material; followed by allowing said amplified nucleic acid material, after denaturation, to hybridize to the probe, attached to the solid surface, to form a double stranded complex, which is detected to indicate the presence of the nucleic acid molecule in the sample.

Stated differently, the method comprises amplifying a nucleic acid molecule, in a sample, by use of two primers in a polymerase chain reaction in the presence of a single stranded nucleic acid probe complementary to said molecule, to produced amplified nucleic acid material, wherein said probe is attached to a solid surface by a dendron, allowing said amplified nucleic acid material, after denaturation, to hybridize to said probe to form a double stranded complex, and detecting said complex.

The use of a cell or tissue containing sample in an amplification reaction, such as PCR, may be performed by any means known to the skilled, person. There have been various attempts to amplify gene sequences of interest directly from cells and tissues (Chen, S and Evans, G A, *Biotechniques* 8:32-33, 1990; Ohhara, M. et al. *Biotechniques* 17:726-728, 1994). As one non-limiting example, Novagen described buffer mixtures that allows direct PCR of blood samples. The Novagen mixtures include BloodDirect buffer 1 and BloodDirect Buffer A (for human blood), or BloodDirect Buffer B (for mouse blood), are mixed with deoxynucleotides, primers, Taq thermostable DNA polymerase, anticoagulant, and a blood sample for successful amplification of a desired DNA sequence by PCR (see Novagen User Protocol TB404). Similar approaches can be used for direct PCR from other cell types and also from tissues. Non-limiting examples of other cell types as the source of a nucleic acid molecule (DNA or RNA) for use in the disclosed disclosure include those of a human patient or animal subject as well as plant cells, lower eukaryotic cells, non-eukaryotic cells, and prokaryotic cells. The cells may be present in a variety of possible samples, including a biological fluid like blood, serum, saliva, urine, and saliva; a water, air, or soil sample from the environment; a clinical specimen; and a forensic sample. In other embodiments, the nucleic acid molecule to be detected is in a cell-free form. Non-limiting examples include nucleic acid molecules in a virus or viral particle, such as an RNA virus or viral particle.

In some embodiments, the disclosure provides a method for detecting a nucleic acid molecule in a sample by use of an immobilized probe as the "capture probe." The method may comprise amplifying a nucleic acid molecule, in a sample, by the polymerase chain reaction (PCR) in the presence of a single stranded nucleic acid probe complementary to the nucleic acid molecule (along with a second nucleic acid primer for PCR), to produced amplified nucleic acid material. The probe (or "capture probe") is directly or indirectly immobilized, or otherwise attached to a solid surface, through its 5' or 3' end by a dendron or other structures such as a silanated surface with functional end group of amine, aldehyde, epoxy, etc. for attachment of a nucleic acid probe. The probe may be complementary to the sequence in any part (or even the whole) of a strand synthesized during PCR.

After amplification, the amplified nucleic acid material is allowed, after denaturation, to hybridize to the immobilized probe to form a double stranded complex. The complex can then be detected and analyzed by any suitable means known to the skilled person.

In other embodiments, a gene amplification reaction such as PCR is conducted in a chamber (on a chip slide) containing an area of capture probes immobilized on top of dendrons or another chemical structure. Subsequent hybridization is carried out in the same chamber. The slide is washed, scanned, and the results analyzed. In further embodiments, a biological sample is added to a PCR mixture, and the mixture is added to a chamber (of a chip slide) assembled on an area that contains capture probes immobilized on dendrons or another chemical structures. The capture probes are directly or indirectly linked to a solid support, such as a dendron, through the 5' or 3' end of the probes. After PCR, hybridization with the capture probes proceeds without any further treatment. Following hybridization, the slide is washed and scanned, and the results are analyzed.

The cells of a sample used in a disclosed method are optionally lysed or permeabalized by means known to the skilled person to facilitate the amplification reaction. Non-limiting examples include a detergent, like NP-40 (also known as NP40 or Nonidet P40), to lyse cells and deoxycholate to permeable cells. The in situ methods used for PCR on tissue slices may also be adapted and used. In alternative embodiments, cells may be ruptured by simply heating them at a high temperature, such as by heating in a microwave as a non-limiting example.

As described above, a combination of direct gene amplification from cells and gene amplification on the surface of capture probes on a gene chip makes "one step diagnosis of gene" possible via a gene chip.

Preparation of PCR Reaction Mixture

In some embodiments, a portion of a solution, such as a supernatant described herein as a non-limiting example, containing denatured DNA is added to a PCR reaction mix. The PCR mixture consists of two oligonucleotide primers that are complementary to the two ends of a target region of a double-stranded DNA to be amplified, 4 deoxynucleotide triphosphates, one or more detectably labeled deoxynucleotide triphosphate, and a thermostable DNA polymerase. Of course the primers may be selected to amplifying all or part of a papillomavirus or hepadnavirus nucleic acid sequence as described herein.

In some cases, the labeled deoxynucleotide triphosphate may be a Cy3- or Cy5-labeled deoxynucleotide triphosphate, a biotin-labeled deoxynucleotide triphosphate, or any other form of detectable label that may be used for labeling of amplified DNA. In other instances, labeled primers may be used to label amplified DNA.

The PCR mixture is transferred to a chamber assembled on, and exposed to, the surface of a chip slide which has immobilized oligonucleotide capture probes as described herein. The slide is placed in, or otherwise operably arranged with, a thermocycler. PCR and hybridization may be carried out in the chamber without changing solutions. In light of the temperatures used in PCR, the hybridization to immobilized probes may occur without a separate act of denaturation of the amplified material. But of course, the use of such an act may optionally be employed followed by reduction in temperature to allow hybridization to occur. After hybridization, the chamber may be removed, and the slide may be washed and inserted into a laser scanner for detecting signals present on the slide.

Simultaneous Amplification and Hybridization

As described herein, the disclosure includes methods wherein the amplification reaction is conducted in the presence of an immobilized probe on a solid substrate. In some embodiments, the methods may be considered to comprise simultaneous amplification (such as PCR) and hybridization reactions. These methods may be advantageously used to avoid the need for separate, and sequential, amplification and then hybridization to an immobilized probe on a solid substrate. The amplification and hybridization may occur on a solid support, such as a chip, slide, or chamber, of the disclosure.

To begin amplification, the reaction volume is transferred to be in contact or otherwise exposed to an immobilized probe on a solid substrate of the disclosure. Optionally, the solid substrate may comprise two different, and non-complementary, probes to hybridize to both strands of the amplified material. In other embodiments, the solid substrate may comprise more than one probe to hybridize to more than one amplified material from a papillomavirus or hepadnavirus nucleic acid.

Hybridization to immobilized probes is facilitated by the denaturing, annealing, and strand extension temperatures used in a PCR reaction. Alternatively, the amplified nucleic acid material in the reaction volume may be converted to a single stranded form. The conversion may be by denaturation of double stranded material after completion of the amplification reaction. In some embodiments, the denaturation is by the use of increased temperature, by heating the solid substrate. After heating to denature double stranded nucleic acids, the temperature of the solid substrate may be lowered, optionally in a controlled manner, to allow hybridization to occur.

Thus the disclosed disclosure also includes a method for detecting a nucleic acid molecule, in a sample, by amplifying the molecule by PCR in the presence of a probe, and then hybridizing it to a probe immobilized to a solid substrate as described herein. In some embodiments, the amplification of the molecule is used to produce amplified nucleic acid material that is in contact with a solid substrate comprising a single stranded nucleic acid probe, attached to the solid substrate by a dendron.

As described herein, the probe is complementary to at least one strand of an amplified papillomavirus or hepadnavirus sequence. Alternatively, the solid substrate may comprise more than one probe that are complementary to more than one papillomavirus, or more than one hepadnavirus, sequence. In some embodiments, the papillomavirus is an HPV. In other embodiments, the more than one probe may hybridize to more than one HPV, or more than one hepadnavirus, sequence. The sequences of the more than one probes may be selected or designed to not interfere with each other during hybridization to the amplified material.

The amplified nucleic acid material forms a double stranded complex with the immobilized probe(s), and the complex is detected to indicate the presence of the nucleic acid molecule in the sample.

Embodiments of these methods include a combined direct PCR and hybridization assay having the following: (1) slide; (2) the slide coated with dendrons or other chemicals; (3) capture probes linked to the dendrons or other chemicals through the 5' or 3' ends of the probes, (4) a chamber assembled around an area that contains the linked capture probes, (5) adding biological sample to a PCR reaction mixture, (6) performing PCR and hybridization simultaneously such that the PCR reaction products present in the chamber, and exposed to the probes, without the need for transfer. The slide is washed, scanned, and the results analyzed.

Exemplification of Immobilization

The disclosed chips and slides are non-limiting examples of solid support substrates which may be used in the practice of the disclosure. Any suitable solid support material may be used. Non-limiting examples include substrates such as oxidized silicon wafer, silica, fused silica, and glass slide.

A dendron which is coated on the surface of substrate in this disclosure is a kind of dendrimer. Dendrimers are highly branched polymers with uniform size and molecular weight as well as a well-defined structure. They consist of a central multifunctional core, multifunctional repeating unit attached around the core, and a terminal or end group. According to their shape, they are divided into two types. The first one has a circular or elliptic shape of which repeating units are regularly stretched from a core, whereas the second type has a conic shape of which repeating units are directionally stretched from a core. The second type is generally called as dendron.

Dendrons having nine branches are mainly used to exemplify the modification of a surface of a solid substrate in this disclosure. The dendron, N-Cbz-[1]amine-[9]acid, described in Oh, S J. et al, Nucl. Acid Res. 2005, 33(10), e90 (and published U.S. Patent Application 2005/0037413) is a non-limiting example of a dendron that may be used.

This dendron molecule was designed for efficient immobilization via covalent binding to the substrate, facile deprotection, intact reactivity of the amine at the apex (of the conical shape), and low nonspecific binding of oligonucleotide or polynucleotide. Various biological molecules such as a nucleic acid probe may be attached to the amine group at the apex of a dendron. Non-limiting examples of attached molecules include polynucleotides, oligonucleotides and PCR products. As reported in Korean patent 10-0383080-0000 and published U.S. Patent Application 2005/0037413, the amines at the apex of among dendrons maintain mesospacing. Therefore, the biological molecules linked to each amine will also maintain mesospacing thus reducing steric hinderance among the biological molecules. In some embodiments, the dendrons on a substrate may be spaced at regular intervals, such as that of about 0.1 nm, about 10 ran, or about 100 nm. As a result, the probes immobilized via the dendrons are also spaced at regular intervals. This also results in dramatic reduction of noise in the analysis of gene sequences by DNA chip (see Oh as cited above).

In addition to the dendron described above, other dendrons with different numbers of branches may also be used in the practice of the disclosed disclosure. Non-limiting examples include a dendron with from about 3 to about 27 branches. Also, other chemical structures that allow immobilization of biomolecules at the apex of cone shaped polymers can be used for the direct and consecutive gene amplification and hybridization described above. The immobilization may be via a covalent bond that is readily cleaved so that the immobilization is reversible.

Immobilized Probes and Primers

The biomolecules used for the combined gene amplification and hybridization described in this disclosure include capture probes of single-stranded polynucleotides or oligonucleotides, such as DNA or PNA, of about 15 to about 70 nucleotides in length that are sufficiently complementary to the nucleic acid (DNA) sequences in biological samples to be analyzed. The nucleic acid (DNA) sequences that are sufficiently complementary to the capture probes may be any regardless of the source. In some embodiments, a capture probe comprises a sequence that is unique to a molecule amplified from a sample described herein. The sequence may contain at least about 16, at least about 18, at least about 20, at least about 22, at least about 24, at least about 26, at least about 28, at least about 30, or at least about 32 consecutive basepairs of a sequence that is not found in other molecules present with the amplified molecule. Other embodiments are polynucleotides of at least or about 50, at least or about 100, at least about or 150, at least or about 200, at least or about 250, at least or about 300, at least or about 350, at least or about 400, at least or about 450, or at least or about 500 consecutive bases of a sequence that is not found in other gene sequences. The term "about" as used in the preceding sentence refers to an increase or decrease of 10% from the stated numerical value. Alternatively, a polynucleotide probe may contain minor mismatches (e.g. via the presence of mutations) which do not affect hybridization to the nucleic acids of a sample.

The probe sequence may be to either strand of a double-stranded sequence. A probe may thus hybridize to the "coding" or "non-coding" strand of a double-stranded sequence. Alternatively, and in the applicable cases, a probe may hybridize to the "+" or "−" strand of a nucleic acid sequence as understood by the skilled person.

To detect papillomavirus nucleic acids, a probe of the disclosure is complementary to a part of a papillomavirus nucleic acid sequence. The sequence may be any of the numerous papillomavirus, or human papillomavirus (HPV), sequences known to the skilled person. Non-limiting embodiments include HPV types that are sexually transmitted or those which cause growths in the genital area. These include types that are oncogenic or carcinogenic. Non-limiting embodiments include those involved in cervical cancer, or cancers of the anus, vulva, vagina, penis and some cancers of the oropharynx (the middle part of the throat that includes the soft palate, the base of the tongue, and the tonsils). Additional non-limiting examples include HPV types 16, 18, 31, 33, 35, 39, 45, 51, 52, 56, 58, 59, and 68. Alternatively, the HPV is one which causes genital or other warts, such as types HPV-6 and HPV-11.

In some embodiments, the probe sequence may be one of those used in the Digene test, such as the probe to HPV type 6, 11, 42, 43 or 44, or probe to HPV type 16, 18, 31, 33, 35, 45, 51, 52, or 56. Non-limiting examples include the HPV type 16 probe 5'-CTCTGGGTCTACTGCAAATTTAGCCAGTT-3' (SEQ ID NO: 3) and the HPV type 18 probe 5-CACAGG-TATGCCTGCTTCACCTG-3' (SEQ ID NO: 8).

Additional non-limiting examples of HPV sequences to detect include those in FIGS. 10 and 11 as well as the HPVs in Table 1 below. In many cases, all or part of the L1 gene of an HPV is amplified and detected as disclosed herein.

TABLE 1

Human papillomavirus genotypes

| Virus | Type | NCBI[1] Accession # | Region sequenced |
|---|---|---|---|
| Human papillomavirus | 1a | V01116 | Complete |
| Human papillomavirus | 2a | X55964 | Complete |
| Human papillomavirus | 3 | X74462 | Complete |
| Human papillomavirus | 4 | X70827 | Complete |
| Human papillomavirus | 5b | D90252 | Complete |
| Human papillomavirus | 6 | AF092932 | Complete |
| Human papillomavirus | 7 | X74463 | Complete |
| Human papillomavirus | 8 | M12737 | Complete |
| Human papillomavirus | 9 | X74464 | Complete |

TABLE 1-continued

Human papillomavirus genotypes

| Virus | Type | NCBI[1] Accession # | Region sequenced |
|---|---|---|---|
| Human papillomavirus | 10 | X74465 | Complete |
| Human papillomavirus | 11 | M14119 | Complete |
| Human papillomavirus | 12 | X74466 | Complete |
| Human papillomavirus | 13 | X62843 | Complete |
| Human papillomavirus | 14d | X74467 | Complete |
| Human papillomavirus | 15 | X74468 | Complete |
| Human papillomavirus | 16 | K02718 | Complete |
| Human papillomavirus | 17 | X74469 | Complete |
| Human papillomavirus | 18 | X05015 | Complete |
| Human papillomavirus | 19 | X74470 | Complete |
| Human papillomavirus | 20 | U31778 | Complete |
| Human papillomavirus | 21 | U31779 | Complete |
| Human papillomavirus | 22 | U31780 | Complete |
| Human papillomavirus | 23 | U31781 | Complete |
| Human papillomavirus | 24 | U31782 | Complete |
| Human papillomavirus | 25 | X74471 | Complete |
| Human papillomavirus | 26 | X74472 | Complete |
| Human papillomavirus | 27 | X74473 | Complete |
| Human papillomavirus | 28 | U31783 | Complete |
| Human papillomavirus | 29 | U31784 | Complete |
| Human papillomavirus | 30 | X74474 | Complete |
| Human papillomavirus | 31 | J04353 | Complete |
| Human papillomavirus | 32 | X74475 | Complete |
| Human papillomavirus | 33 | M12732 | Complete |
| Human papillomavirus | 34 | X74476 | Complete |
| Human papillomavirus | 35 | M74117 | Complete |
| Human papillomavirus | 36 | U31785 | Complete |
| Human papillomavirus | 37 | U31786 | Complete |
| Human papillomavirus | 38 | U31787 | Complete |
| Human papillomavirus | 39 | M62849 | Complete |
| Human papillomavirus | 40 | X74478 | Complete |
| Human papillomavirus | 41 | X56147 | Complete |
| Human papillomavirus | 42 | M73236 | Complete |
| Human papillomavirus | 43 | U12504 | L1 |
| Human papillomavirus | 44 | U31788 | Complete |
| Human papillomavirus | 45 | X74479 | Complete |
| Human papillomavirus | 47 | M32305 | Complete |
| Human papillomavirus | 48 | U31789 | Complete |
| Human papillomavirus | 49 | X74480 | Complete |
| Human papillomavirus | 50 | U31790 | Complete |
| Human papillomavirus | 51 | M62877 | Complete |
| Human papillomavirus | 52 | X74481 | Complete |
| Human papillomavirus | 53 | X74482 | Complete |
| Human papillomavirus | 54 | U37488 | Complete |
| Human papillomavirus | 55 | U31791 | Complete |
| Human papillomavirus | 56 | X74483 | Complete |
| Human papillomavirus | 57 | X55965 | Complete |
| Human papillomavirus | 58 | D90400 | Complete |
| Human papillomavirus | 59 | X77858 | Complete |
| Human papillomavirus | 60 | U31792 | Complete |
| Human papillomavirus | 61 | U31793 | Complete |
| Human papillomavirus | 62 | U12499 | L1 |
| Human papillomavirus | 63 | X70828 | Complete |
| Human papillomavirus | 64 | U12495 | L1 |
| Human papillomavirus | 65 | X70829 | Complete |
| Human papillomavirus | 66 | U31794 | Complete |
| Human papillomavirus | 67 | U12492 | L1 |
| Human papillomavirus | 68 | M73258 | LCR, E6, E7, E1, L1, L2 |
| Human papillomavirus | 69 | U12497 | L1 |
| Human papillomavirus | 70 | U21941 | Complete |

[1]National Center for Biotechnology Information (information available on the worldwide web at ncbi.nlm.nih.gov).

Of course the primer sequences used in the practice of the disclosure may be designed to amplify all or part of any papillomavirus nucleic acid, including one or more of the above or in the Figures. In most embodiments, the primers (forward and reverse) will amplify a region that is complementary to all or part of a probe sequence. In other embodiments, the primers amplify the same region in more than one HPV type but with different sequences within the amplicon such that probes specific for the different sequences may be used to detect which HPV type is present.

As one non-limiting example, the forward primer (GP4F) is 5'-GATGGTGATATGGTWSATACAGGMTWTGG-3' (SEQ ID NO: 4) and the reverse primer (GP4R) is 5'-GMRTCAGAGGTTACMATAGARCCACTWGG-3' (SEQ ID NO: 5) where W denotes mixture of A and T; S that of C and G; M that of A and C; and R that of A and G.

To detect hepadnavirus nucleic acids, a probe of the disclosure is complementary to a part of a hepadnavirus nucleic acid sequence. The sequence may be any of the numerous hepadnavirus, such as HBV, sequences known to the skilled person. Non-limiting embodiments include HBV types that considered "wildtype" as well as "mutant." Further embodiments include those of an orthohepadnavirus, avihepadnavirus, or other vertebrate hepadnavirus. Non-limiting examples of HBV sequences to detect include those in Tables 2 and 3 below, including mutants of HBV type C.

TABLE 2

Genotypes of Hepatitis B Virus

| HBV Subtype | Genebank Accession# | Blast GI# | Title | Length |
|---|---|---|---|---|
| A | X02763 | 59418 | Hepatitis b virus genome (serotype adw2) | 3221 |
|   | X51970 | 1155012 | Hepatitis B virus (HBV 991) complete genome | 3221 |
|   | AF090842 | 5114084 | Hepatitis B virus strain G5.27295, complete genome | 3221 |
| B | D00329 | 221497 | Hepatitis B virus subtype ADW DNA, complete genome, clone: pJDW233. | 3215 |
|   | AF100309 | 4323201 | Hepatitis B virus strain 56, complete genome | 3215 |
|   | AB033554 | 6063442 | Hepatitis B virus DNA, complete genome, isolate: RTB299. | 3215 |
| C | X04615 | 59585 | Hepatitis B virus genome, subtype ayr | 3215 |
|   | M12906 | 474959 | Hepatitis B virus subtype adr, complete genome. | 3215 |
|   | AB014381 | 3582357 | Hepatitis B virus genomic DNA, complete sequence, isolate 22Y04HCC. | 3215 |
| D | X65259 | 59439 | Hepatitis B virus (ayw, patient E) genes PreS1, PreS2, PreC, C, X and polymerase | 3182 |
|   | M32138 | 329667 | Hepatitis B virus variant HBV-alpha1, complete genome. | 3182 |
|   | X85254 | 736003 | Hepatitis B virus genome (PreS1, PreS2, S, PreC, C, X genes and polymerase) | 3182 |
| E | X75657 | 452617 | Human hepatitis virus (genotype E, Bas) preS1, preS2, S, C, X, antigens, core antigen, X protein and polymerase | 3212 |

TABLE 2-continued

Genotypes of Hepatitis B Virus

| HBV Subtype | Genebank Accession# | Blast GI# | Title | Length |
|---|---|---|---|---|
| | AB032431 | 6691492 | Hepatitis B virus genomic DNA, complete sequence, isolate: HBV/E-Ch195. | 3212 |
| F | X69798 | 59422 | Hepatitis B virus, subtype adw4 genes | 3215 |
| | AB036910 | 11191875 | Hepatitis B virus (genotype F) genomic DNA, complete genome, isolate: VNZ8251. | 3215 |
| | AF223965 | 12247041 | Hepatitis B virus strain C-1858 isolate sa16, complete genome. | 3215 |
| G | AF160501 | 6983934 | Hepatitis B virus strain IG29227, complete genome | 3248 |
| | AB064310 | 18146661 | Hepatitis B virus DNA, complete genome, clone: USG769. | 3248 |
| | AF405706 | 19849032 | Hepatitis B virus isolate 235/01, complete genome | 3248 |
| H | AY090454 | 22135696 | Hepatitis B virus strain 1853Nic, complete genome | 3215 |
| | AY090457 | 22135711 | Hepatitis B virus strain 2928Nic, complete genome | 3215 |
| | AY090460 | 22135726 | Hepatitis B virus strain LAS2523, complete genome | 3215 |

TABLE 3

Mutants of Hepatitis B Virus type 3

| Virus | Type | Mutant | Genebank Accession Information |
|---|---|---|---|
| Hepatitis B virus | C | 80L | DQ536411 |
| Hepatitis B virus | C | 80I | EF645264 |
| Hepatitis B virus | C | 85C | AB111117 |
| Hepatitis B virus | C | 85R | EU306673 |
| Hepatitis B virus | C | 169I | L08805 |
| Hepatitis B virus | C | 173V | AB206817 |
| Hepatitis B virus | C | 180L | AB247916 |
| Hepatitis B virus | C | 180M | AB195957 |
| Hepatitis B virus | C | 181A | D16666 |
| Hepatitis B virus | C | 181T | AB247916 |
| Hepatitis B virus | C | 181V | DQ343156 |
| Hepatitis B virus | C | 184T | EF626034 |
| Hepatitis B virus | C | 194A | AB198079 |
| Hepatitis B virus | C | 202S | AB111118 |
| Hepatitis B virus | C | 204I | AB195954 |
| Hepatitis B virus | C | 204L | AF074449 |
| Hepatitis B virus | C | 204M | AB033552 |
| Hepatitis B virus | C | 204V | AB195951 |
| Hepatitis B virus | C | 215Q | AB014376 |
| Hepatitis B virus | C | 215H | DQ089785 |
| Hepatitis B virus | E | 215R | X75664 |
| Hepatitis B virus | C | 233I | AB206817 |
| Hepatitis B virus | C | 233V | AF330110 |
| Hepatitis B virus | C | 236N | AB014376 |
| Hepatitis B virus | C | 236T | EF378599 |
| Hepatitis B virus | D | 236S | EU027433 |
| Hepatitis B virus | C | 237P | AB205124 |
| Hepatitis B virus | C | 238N | AB026815 |
| Hepatitis B virus | C | 250M | AB014377 |

Preparation of Solid Medium

Coating of a solid substrate or medium, like a glass slide or microarray, with dendron may be by a suitable means known to the skilled person. As a non-limiting example, the substrate is first coated with dendron, and capture probes are linked to the apex of the dendron. The coating may be to prepare surfaces on the substrate or medium for immobilization of a polynucleotide probe or primer as described herein.

In some embodiments, the surface is that of an array or "microarray", which refers to a linear or two-dimensional or three dimensional (and solid phase) array of discrete surface regions. Each region has a defined area that is formed on the surface of a solid support such as, but not limited to, glass, plastic, or synthetic membrane. In some cases, each region is a surface of a chamber as described herein. The density of the discrete regions on a microarray may be determined by the total number of immobilized polynucleotides to be detected on the surface of a single solid phase support, such as of at least about 50/cm$^2$, at least about 100/cm, or at least about 500/cm, up to about 1,000/cm or higher. An array may contain less than about 500, about 1000, about 1500, about 2000, about 2500, or about 3000 regions of immobilized polynucleotides in total. Because the position of each particular group of probes in the array is known, the identities of a sample polynucleotides can be determined based on their binding to a particular position in the microarray. As an alternative to the use of a microarray, an array of any size may be used in the practice of the disclosure.

The regions may be in the form of spots with a diameter of about 100 to about 500 µm, such as about 200 to about 300 µm or about 240 µm. While each region generally contains one probe type with the same sequence, several regions with the same probe type may be on the same solid surface. This allows the same probe type to be used in parallel assays. In some embodiments, the regions may be spaced apart from each other by about 100 to about 500 µm, such as from about 200 to about 300 µm or about 280 µm. The process of coating dendron is as follows. The substrate such as glass slide is washed and dried. The washed slide is dipped into silane solution to form a silanated surface. After silanation, the substrate is washed with an appropriate solvent and dried. The silanated substrate is then dipped into a solvent containing dendron such as N-Cbz-[1]amine-[9] acid and maintained under nitrogen (N$_2$) gas. In the case of N-Cbz-[1]amine-[9] acid, the amine is protected. Therefore, the protective group is removed to expose the amine moiety. After deprotection, the substrate surface is washed with solvent such as methanol. For crosslinking of either the 3' end or 5' end of a capture probe to the exposed dendron amine, the deprotected dendron surface is modified with di(N-succinimidyl)carbonate (DSC). After the substrate is washed with deionized water, capture probe is dissolved in a buffer solution and spotted on a DSC-modified dendron substrate, and reacted for 12 hours under humidity of 85%.

A sealed chamber is constructed that includes the area of the capture probes, and consecutive gene amplification and hybridization is carried out in this chamber. The assembly of the chamber(s) may be on a chip slide. The chamber can be assembled by use of commercially available material (for example, Hyb-Seal Incubation Chambers, Bio-Rad Laboratories). The chamber assembly material is taped on an area of the chip slide that contains the capture probes immobilized on the surface of dendrons. After sample solution for gene amplification is added to the chamber, the top of the chamber is sealed with a cover.

PCR

As described herein, some methods of the disclosure may be practiced by use of direct PCR. For direct PCR, biological materials such as cells, appropriate primers, deoxynucleotide triphosphates, a fluorescent labeled deoxynucleotide triphosphate, appropriate buffer, and thermostable DNA polymerase are premixed. The mixture is added through an injection hole of a chamber that contains an area of capture probes immobilized on the surface of dendrons. PCR is performed in a temperature cycler that can accept slides (for example, PTC Slide Cycler, M J Research, Co.). In the case of direct PCR with the capture probes as primers, the capture probes will be linked to dendron through 5' or 3' end of the DNA or PNA. After PCR, the chamber assembly may be peeled off from the glass slide, and the slide is washed and/or rinsed before being scanned by a confocal laser scanner as described below.

General principles for the determination of PCR temperatures, cycle times, and numbers of cycles are known to the skilled person. As a non-limiting example, the temperature requirements for PCR may be as follows: the temperature range for DNA denaturation (strand separation) is 90-95° C., the temperature for annealing of primers with separated strands of DNA is between 50-65° C., and finally the optimum temperature for elongation of DNA chain from the annealed primer by thermostable DNA polymerase is 70-75° C.

Hybridization Conditions

For hybridization, the temperature for denaturation of PCR product is 90-95° C., and the range of temperature for hybridization of PCR product with the capture probes linked to dendrons is 40-65° C.

In the case of simultaneous PCR and hybridization, and after direct PCR with biological samples, the PCR reaction mixture (in a chamber on a glass slide) may be heated at about 95° C., and hybridization may carried out for about one hour at about 50° C. and about 2 hours at about 45° C., all conditions as non-limiting examples. After hybridization, the chamber is removed and the slide is washed once with 1×SSC+0.1% SDS, once with 0.1×SSC+0.1% SDS and once with 1×SSC, all as non-limiting examples.

Alternatively, the hybridization conditions used maybe at a temperature of about 30 to about 80° C., such as from about 40 to about 70° C., or from about 55 to about 65° C. The hybridization temperature may be adjusted as deemed appropriate by the skilled person based on multiple factors, such as the melting temperature of the probe sequences used. The temperature may also be determined, adjusted, and held relatively constant for each hybridization reaction.

The cycling of temperatures in the practice of the instant disclosure may be by any means known to the skilled person. In some embodiments, a solid substrate, with immobilized capture probes on a surface, of the disclosure is in operative contact with a thermocycler capable of regulating the cycling parameters in the solid substrate. Non-limiting examples of such parameters include temperature, temperature cycle times, and number of temperature cycles. Various thermocyclers are known to the skilled person, including those which are automatic or semi-automatic after selection of cycling parameters like those described above.

Detection Means

While many of the amplification reactions described herein labels the amplified nucleic acid material by inclusion of a fluorescently labeled deoxynucleotide triphosphate in the reaction mixture, other labeling means may be used. One non-limiting example is the use of a radioisotope label. Alternatively, other means may be used to detect the amplified nucleic acid material after immobilization as described herein. Non-limiting examples include electrochemical detection and the use of a double stranded nucleic acid binding agent, such as Sybr Green, which is advantageously used after a wash or rinse step to remove unbound material from a chip or slide surface. Alternative detection means known to the skilled person may also be used.

Non-limiting examples beyond fluorescence include labeling with a radioactive or chemiluminescent moiety or other means based upon a chemical, enzymatic, physico-chemical or antigen-antibody binding process, in some embodiments, a label such as alkaline phosphatase, horseradish peroxidase, β-galactosidase, urease, luciferase, rhodamine, fluorescein, phycoerythrin, luminol, isoluminol, an acridinium ester or a fluorescent microsphere is used as a detectable moiety.

The analysis of the amplified material on a solid substrate may be by any suitable means known to the skilled person. For DNA analysis after hybridization, a general, non-limiting procedure to be followed is by using a commercially available confocal laser scanner for image acquisition and a quantitative microarray analysis software for the fluorescence intensity analysis. The disclosure is not limited to use of a particular analysis method. In a fluorescence intensity analysis method as a non-limiting example, PCR product is labeled with fluorescence by carrying out chain elongation in the presence of deoxynucleotide triphosphate labeled with a fluorescent group. One then determines the level of fluorescence that hybridized to capture probes after hybridization by a laser scanner and computer microarray software analyzes the signals on a DNA chip slide.

Range of Nucleic Acid Molecules Detected

As evident from the above, the disclosed methods may be practiced to detect a viral nucleic acid molecule, such as a papillomavirus or hepadnavirus nucleic acid molecule of interest, in a sample. The nucleic acid molecule may be a DNA molecule.

Kits

The disclosure further provides kits for the amplification and detection of nucleic acid molecules as described herein. A kit will typically comprise one or more reagents to detect nucleic acids as described herein for the practice of the present disclosure. Non-limiting examples include polynucleotide primers for amplification, one or more enzymes used in the methods of the disclosure, and one or more tubes for use in the practice of the disclosure. In some embodiments, the kit will include an array or microarray, or solid media capable of being assembled into an array or microarray, for the detection of amplified molecules as described herein. Other structures that may be included are those of the chamber on a solid support for conducting the amplification and hybridization.

A kit of the disclosure may also include instructional materials disclosing or describing the use of the kit or one or more components thereof in a method as described herein. A kit may also include additional components to facilitate the particular application for which the kit is designed. Thus, for example, a kit may additionally contain means of detecting a label (e.g. enzyme substrates for enzymatic labels, filter sets to detect fluorescent labels, or the like). A kit may additionally include buffers, salts, solutions, and other reagents recognized for use in a method of the disclosure.

Having now provided a written description, the same will be more readily understood through reference to the following examples which are provided by way of illustration, and are not intended to be limiting of the disclosure, unless specified.

EXAMPLES

Example 1

Verification of Capture Probes for HPV Assay

The following capture probes and primers for HPV were synthesized:

```
Forward primer (GP4F):
5' Cy3-GATGGTGATATGGTWSATACTGGMTWTGG 3'
(SEQ ID NO: 6);

Reverse primer (GP4R):
5' Cy3-GMRTCAGAGGTAACMATAGARCCACTWGG 3'
(SEQ ID NO: 7);

HPV 16 probe:
5' CTCTGGGTCTACTGCAAATTTAGCCAGTT 3'
(SEQ ID NO: 3);

HPV 18 probe:
5' CACAGGTATGCCTGCTTCACCTG 3'
(SEQ ID NO: 8);

Marker position probe:
5' TTTACACCTAGTGGCTCTATGGTGTCCTCT 3'
(SEQ ID NO: 9).
```

M denotes mixture of A and C; R that of A and G; W that of A and T; S that of C and G.

The primers and the capture probes were derived from the L1 region of HPV as described in Albrecht et al. *J. Virol Methods* 137:236-244, 2006 and a published Korean patent document (10-2006-0019042). The underlined sequence in the Marker position probe is complementary to the underlined sequence of the fluorescent reverse primer. Therefore, the marker position probe will always hybridize with the reverse primer and will be labeled positive in the final DNA slide. The capture probes were crosslinked to dendron slide as described herein.

To verify the specificity of the capture probes, the HPV sequences for HPV16 and HPV18 were amplified by PCR from the plasmids purified from the following *E. coli* strains. For HPV16, the ATCC 45113 strain, and for HPV18, the ATCC45152 strain (purchased from American Type Culture Collection) were used.

PCR mixture (30 µl) containing 3 µl of 10× reaction buffer, 1.4 µl of 10 mM each of 4 deoxynucleotide triphosphate, Taq polymerase (5 U/µl), 0.4 µl of Cy3-forward primer (100 pmol/µl), 0.1 ml of Cy3-reverse primer (100 pmol/µl), 23 µl of deionized water, and 2 µl of plasmid was used.

PCR was carried out as follows: heating at 94° C. for 5 min and 40 cycles of 1 min at 94° C., 1 min at 50° C., 1 min at 72° C. and finally 5 min at 72° C.

The PCR product was verified by gel electrophoresis and the mixture, without purification of the product, was transferred to the chamber assembled on the dendron glass slide which contains the immobilized capture probes. Hybridization was carried out as follows: heating at 94° C. for 5 min for denaturation of the PCR product and annealing with the capture probes at 50° C. for 3 hours. The chamber was peeled off and the slide was dipped for 5 min each, in sequence, in the following solutions: 1×SSC+0.1% SDS, 0.1×SSC+0.1% SDS and 1×SDS. The final slide was rinsed with deionized water and dried.

Figure 2:
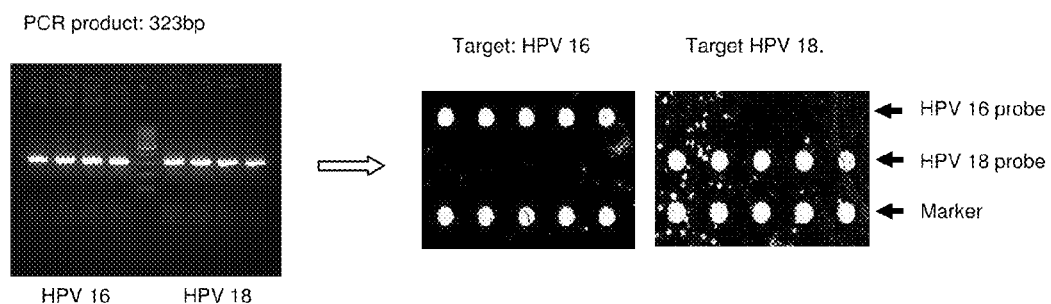

The dried slide was inserted into a laser scanner (Scan Array Express, Perkin Elmer, Co.) and the fluorescent image was scanned and the result was analyzed. As shown in FIG. 2, the capture probes recognized correct HPV sequences.

Example 2

Verification with the Cells Infected with HPV16 and HPV18

Human cervical carcinoma-derived cell line Caski containing HPV16 sequence (ATCC CCl-2), the HeLa S3 containing HPV18 (ATCC CRL-1550), and a leukemia cell line K562 which does not carry HPV sequence (ATCC KCLB-10243), were grown in appropriate culture medium.

Figure 3:
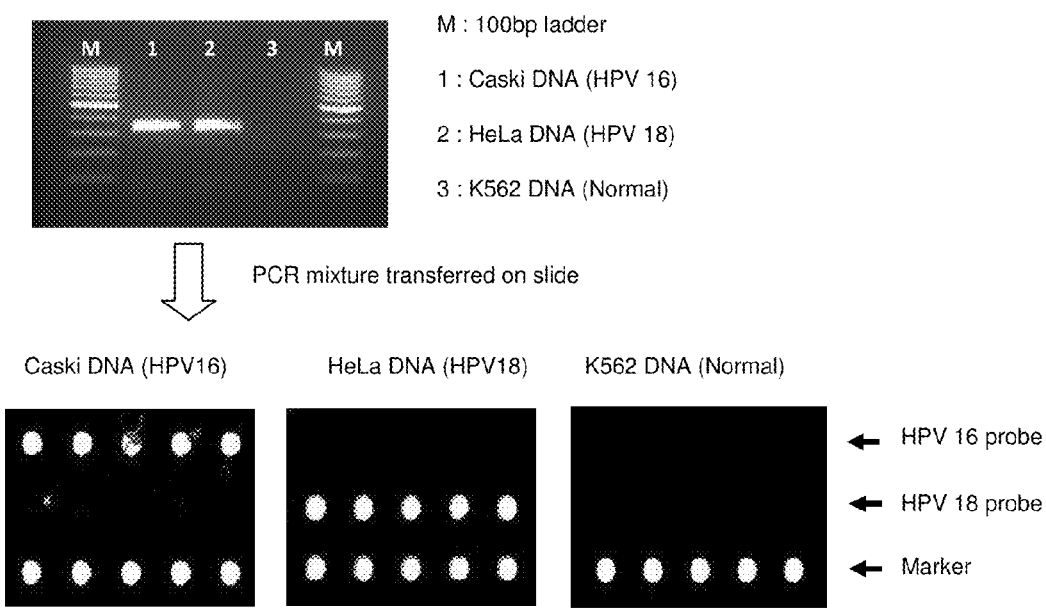
FIG. 3 demonstrates detection of the HPV sequences in infected cells by a DNA chip. The HPV sequence in the genomic DNA of infected cells was amplified by PCR, and the PCR mixture was transferred on DNA chip and hybridized with capture probes.

DNA was extracted from the cell lines described above using G-DEX™ IIc Genomic DNA Extraction Kit (Cell/Tissue), INTRON, Co, Korea). PCR reaction mixture was assembled and PCR was carried out as described in Example 1 and transferred to the chamber assembled on the DNA slide. The slide was incubated in a PCR machine using the hybridization conditions as described in Example 1. The result showed that the HPV sequences in the infected cells can be identified correctly as shown in FIG. 3.

Example 3

Cell Samples Used for PCR in a Tube or on the DNA Chip Surface Gave Similar Results The HPV infected (Caski and HeLa cells) and non-infected (K562 cells) cells were grown. The cells were scrapped from the culture dish and suspended in PBS buffer. The cells (about 10,000 cells) were pelleted in a 1.5 ml Eppendorf tube, and to the pellet was added 50 µl of 5% Chelex-100 resin (Bio-Rad Laboratories). The content of the tube was heated at 95° C. for 5 min and the tube was centrifuged for 5 minutes. The supernatant was saved. Two sets of 30 µl PCR reaction mixtures were prepared with 2 µl each of the supernatant as described in Example 1.

Figure 4:
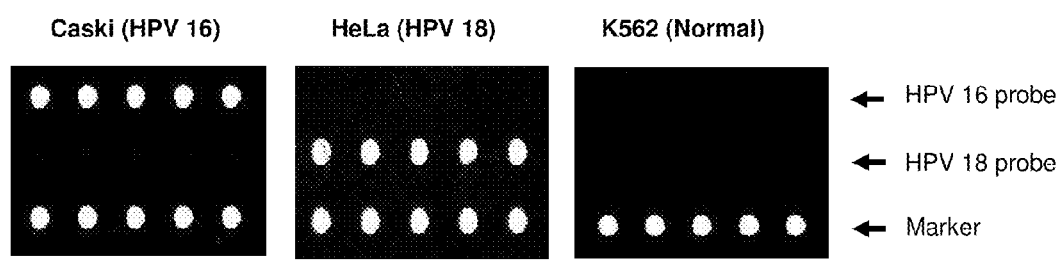
FIG. 4 demonstrates that the cells treated as in FIG. 1 can be used for PCR without purification of DNA, and PCR can be carried out either in a tube or on DNA chip with the same results for detection of HPV sequences by DNA chip.
Figure 4:
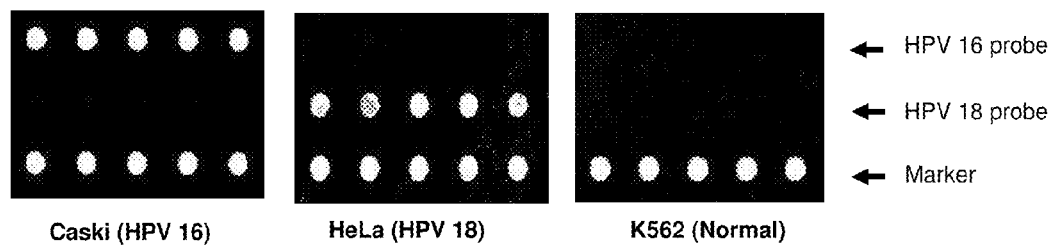

One set of PCR mixture was transferred into a chamber assembled on DNA chip, and PCR and hybridization were carried out under the condition described in Example 1. PCR was carried out in the tubes with another set of reaction mixtures. After PCR the content was transferred into the chamber assembled on DNA slide for hybridization. The results (in FIG. 4) showed that the PCR carried out either in a tube or on the DNA slide gave similar result.

Example 4

Detection of HPV in Clinical Human Cervical Specimens

Cervical samples from human subjects were collected with a Dacron swab and stored in 2 ml of PBS solution in 15 ml conical tube. All of the patients had a history of HPV infection. An aliquot was transferred to a 1.5 ml Eppendorf centrifuge tube and centrifuged for 5 min in a microfuge. To the cell pellet was added 50 µl of Chelex 100-resin, and the sample was heated at 95° C. for 5 min. The heated sample was centrifuged for 5 min. The supernatant was removed and saved.

The PCR mixture (30 µl) was assembled as described in Example 1. The PCR mixture was transferred to a chamber assembled on the surface of dendron glass slide on which the HPV capture probes were crosslinked. The slide was placed on a heating block in a thermocycler. The slide was heated at the same heating cycles described for PCR in Example 1 and the slide was heated at 95° C. for 5 minutes and incubated at 50° C. for 3 hours for hybridization with the capture probes. The chamber was peeled off and the slide was washed as described in Example 1.

Figure 5:
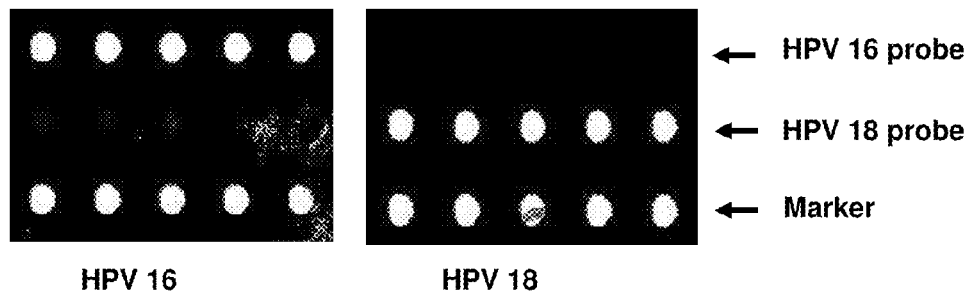
FIG. 5 shows that the cervical cells from human patients infected with either HPV16 or HPV18 can be treated as in FIG. 1, and the supernatant can be amplified by PCR on DNA chip for detection of HPV sequences.

FIG. 5 shows that the HPV type can be identified correctly from the patient's cervical cells by using the integrated process. The HPV sequences of the cervical cells were identified by sequencing the PCR product in separate experiments.

Example 5

Comparison of Dendron and Aldehyde Slides

Figure 6:
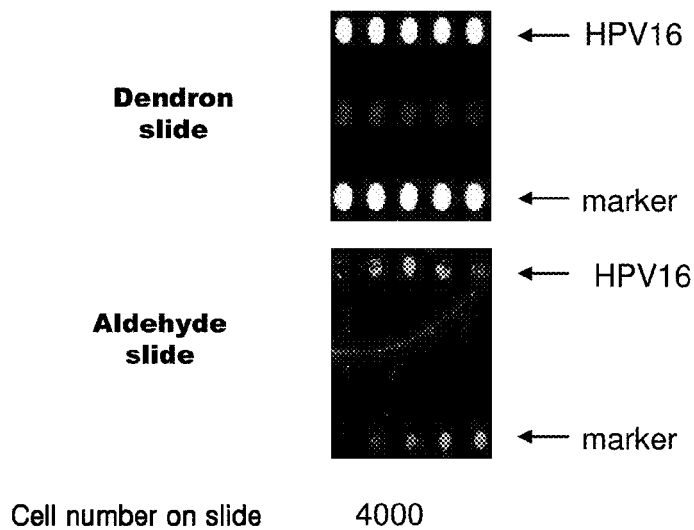
FIG. 6 demonstrates that the dendron surface of DNA chip is beneficially used over an aldehyde slide for probe immobilization in the integrated process.

Caski cells (infected by HPV16) were pelleted in a 1.5 ml Eppendorf centrifuge tubes, and the cell pellet was re-suspended in 50 µl of 5% Chelex 100-resin. The tube was heated at 95° C. and centrifuged. PCR mixture (30 µl) was assembled with 2 µl of the supernatant and transferred to a chamber assembled on DNA slide. PCR and hybridization were carried out as described in Example 1. The performance of dendron slide and commercial aldehyde slide was compared. As shown in FIG. 6, the integrated process only works with the dendron slide.

Example 6

Comparison Between Cells and Purified DNA for Integrated Process

The sensitivity of the detection of HPV sequences was compared between DNA and heated cell samples. DNA was purified from Caski cells by the procedure described in Example 2. In this procedure, the DNA sample was treated with RNase to remove any contaminating RNA. The concentration of DNA solution was appropriately diluted such that when 2 µl was taken, it would correspond to the amount of DNA present in 1000, 100, 10, 1 cells.

Figure 7:
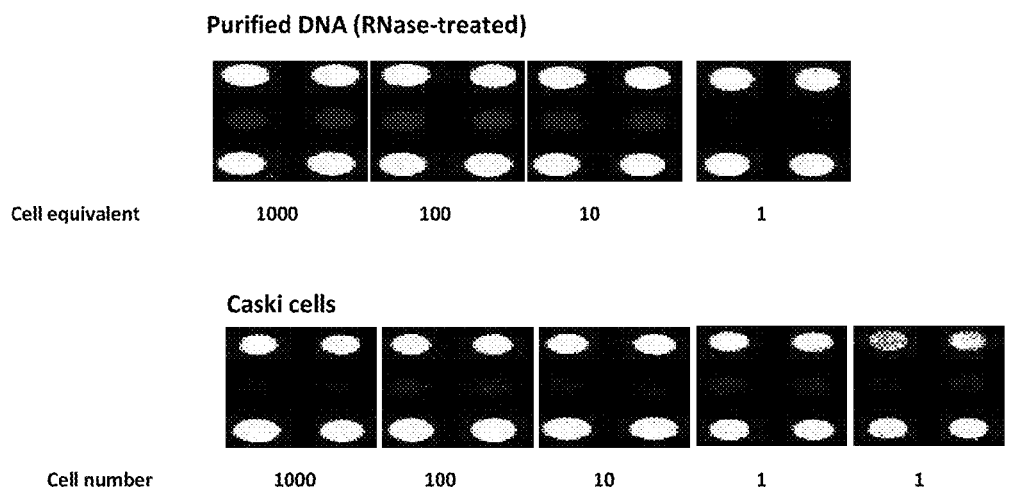
FIG. 7 demonstrates that the dendron chip can identify the HPV sequence from DNA purified from infected Caski cells and from heated Caski cells with very similar sensitivity.

A known stock Caski cells of the known cell number was heated at 95° C. in the presence of Chelex-resin and centrifuged as described in Example 4. The supernatant was saved and appropriately diluted such that when 2 µl was taken it would correspond to 1000, 100, 10, and 1 cells. The DNA and the supernatant from the heated cells were used to assemble PCR mixtures as described in Example 4 and transferred to a chamber on DNA chip slide. PCR and hybridization were carried out as described in Example 4. The result is shown in FIG. 7.

The results show that the purified DNA and the heated cells gave very similar result in detecting the HPV16 sequences. Also, the results show that HPV sequences can be detected with as little as one cell.

Example 7

Identification of Different Types of HPV by DNA Chip

Human patient cervical cells infected by different types of HPV (HPV-6, HPV-11, HPV-16, HPV-18, HPV53, and HPV58) were identified as follows: The DNA extracted from the clinical specimen of cervical cells were amplified by PCR using HPV specific primers and the amplified DNA bands were extracted and sequenced. The cells characterized for the infection by different types of HPV were heated in the presence of Chelex-resin and the supernatant was used for the combined PCR and hybridization on DNA chip as described in Example 4.

The same primers (GP4F and GP4R) used in Example 1 were used, with the following capture probe sequences:

```
HPV-16:      5'CTCTGGGTCTACTGCAAATTTAGCCAGTT 3'
             (same as in Example 1) (SEQ ID NO: 3);

HPV-18:      5' CACAGGTATGCCTGCTTCACCTG 3'
             (same as shown in Example 1)
             (SEQ ID NO: 8);

HPV-53:      5' ACCCGCCCCCTAGCTCTGTATAT 3'
             (SEQ ID NO: 10);

HPV-58:      5' CTGGAAAACTTGGCGAGGCTGT 3'
             (SEQ ID NO: 11);

HPV-6:       5' AAATCGCACGTCTGTAGG 3' (SEQ ID NO: 12);

HPV-11:      5' TGCCTGATGACCTGTTGGTAAAAGG 3'
             (SEQ ID NO: 13);

Marker       5' TTTACACCTAGTGGCTCTATGGTGTCCTCT 3'
position:    (same as in Example 1) (SEQ ID NO: 9).
```

Figure 8:
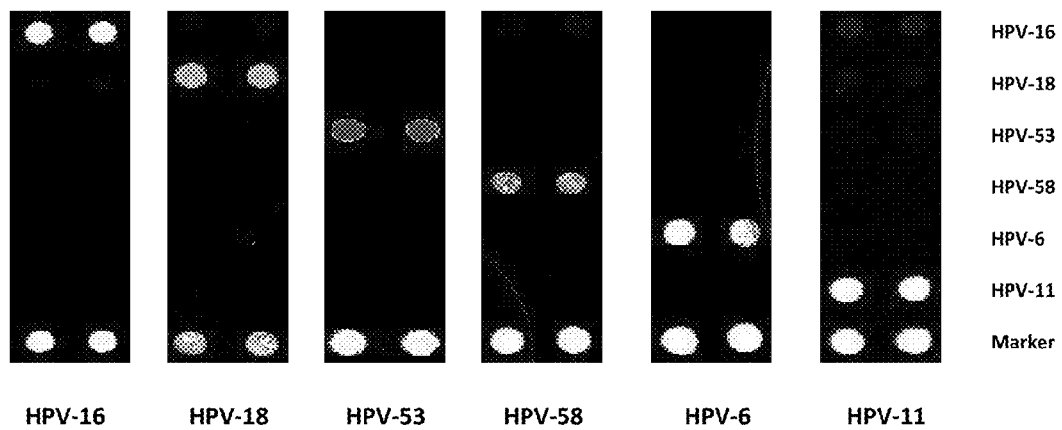
FIG. 8 demonstrates that the dendron DNA chip can identify various types of HPV from the infected human cervical cells without prior purification of DNA.

As shown in FIG. 8, the presence of six different types of HPV (HPV-6, HPV-11, HPV-16, HPV-18, HPV-53, and HPV-58) in the clinical specimen of infected human cervical cells were distinguished.

Example 8

Identification of HVB Sequence in Clinical Specimen of Human Serum

A clinical specimen of serum from a patient infected with HVB was used to demonstrate the integrated protocol for a non-cervical cell sample type as well as for another DNA virus. Serum was diluted with an equal volume of 5% Chelex-resin. The diluted serum was heated at 95° C. for 5 min and centrifuged. A PCR reaction mixture (30 µl) was assembled as follows: 3 µl of 10× buffer, 2 µl of 4 deoxynucleotide triphosphates (mixture of 2.5 mM each of dATP, dGTP, dCTP and 1.5 mM of TTP), 0.75 µl of Cy3-dUTP (1 mM), 0.6 ml of Taq polymerase (5 Units/µl), 1 µl of BVF primer (10 pmol/µl), 2 µl of BVR primer (10 pmol/µl), with 1 µl of the heated serum, and 19.65 µl of H$_2$O. The mixture was transferred to the dendron slide containing the immobilized HVB capture probes, and PCR and hybridization was carried out as described in Example 4.

The primers used were:

```
BVF:    5'-TGGCCAAAATTCGCAGTCCC-3' (SEQ ID NO: 14);

BVR:    5'-TGACATACTTTCCAATCAATAGGTCTA-3'
        (SEQ ID NO: 15);
```

The capture probes used were:

```
BVF233ATA:    5'-ATTTTCTTTYGTCTYTGGGTATACA-3'
              (SEQ ID NO: 16);

BVF233GTA:    5'-TTTCTTTYGTCTYTGGGTGTACA-3'
              (SEQ ID NO: 17);

BVF233GTG:    5'-CTTTYGTCTYTGGGTGTGCA-3'
              (SEQ ID NO: 18);

BVF233ATG:    5'-TTCTTTYGTCTYTGGGTATGCA-3'
              (SEQ ID NO: 19).
```

Figure 9:
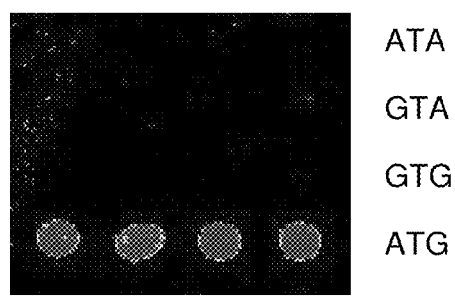
FIG. 9 demonstrates that the dendron DNA chip can identify HVB sequences in a clinical specimen of serum infected by HVB without purification of DNA.

FIG. 9 shows that heated serum can be used in a combined PCR and hybridization process on a dendron DNA slide to identify HBV sequences in a clinical specimen of serum infected by HBV.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for detecting a papillomavirus nucleic acid molecule in a sample, said method comprising:

amplifying a papillomavirus nucleic acid molecule, in a biological sample, by use of a pair of primers in a polymerase chain reaction (PCR), to produce amplified nucleic acid material which is in a PCR reaction mix, in the presence of a single stranded nucleic acid probe that is complementary to said amplified nucleic acid material and is immobilized via attachment to the apex of a conical dendron that is attached to a solid surface by the base of said conical dendron, completing the last cycle of the PCR to produce amplified nucleic acid material, denaturing said amplified nucleic acid material in the presence of said PCR reaction mixture to form a denatured mixture in the presence of the immobilized probe and attached conical dendron, allowing the denatured amplified nucleic acid material, within the same PCR reaction mixture, to hybridize to said probe to form a double stranded complex in the presence of said denatured mixture, and detecting said complex attached to said solid surface.

2. The method of claim 1 wherein said papillomavirus is a human papillomavirus (HPV).

3. The method of claim 2 wherein said HPV is an HPV type 16 or HPV type 18.

4. The method of claim 2 wherein said HPV is selected from an HPV of type 6, type 11, type 31, type 33, type 35, type 39, type 40, type 42, type 43, type 44, type 45, type 51, type 52, type 56, type 58, type 59, or type 68.

5. The method of claim 1 wherein said solid surface is in contact with a thermocycler capable of regulating the temperature, temperature cycle times, and number of temperature cycles in said solid surface.

6. The method of claim 5 wherein said regulating is automatically controlled by said thermocycler.

7. The method of claim 1 wherein said sample comprises whole blood, blood serum, one or more cells susceptible to papillomavirus infection, or a papillomavirus or papillomavirus viral particle; or
   said papillomavirus nucleic acid molecule is in a cell-free sample; or said nucleic acid molecule is in a papillomavirus viral particle, in said sample; or
   said papillomavirus nucleic acid molecule is a DNA molecule; or
   a cellular genomic DNA molecule.

8. The method of claim 1 wherein said detecting comprises contacting said complex with a detectable label which binds double stranded DNA to form a detectably labeled complex, and detecting the labeled complex; or
   said amplifying comprises use of a primer, or nucleotide triphosphate, which is attached to a detectable label, optionally fluorescent, and incorporated into said amplified nucleic acid material, and said detecting comprises detection of said label.

9. The method of claim 1 wherein said primers comprise more than one pair to amplify more than one papillomavirus to produce more than one amplicon, and said solid surface comprises more than one immobilized probe which hybridizes to the more than one amplicon.

10. The method of claim 9 wherein said more than one pair of primers amplify more than one HPV, and said more than one immobilized probe which hybridizes to more than one HPV amplicon.

11. The method of claim 10 wherein said more than one HPV comprises HPV type 16 and HPV type 18, and said more than one immobilized probe hybridizes to HPV type 16 and HPV type 18 amplicons.

12. The method of claim 1 wherein said sample is obtained from a cell containing sample.

13. The method of claim 12 wherein said sample is the supernatant from a cell containing sample that has been heated and centrifuged.

14. The method of claim 1 wherein said sample comprises nucleic acid material from a cell susceptible to papillomavirus infection or suspected of being infected with a papillomavirus.

15. The method of claim 14 wherein said cell is a human cell.

16. The method of claim 15 wherein said cell is a cervical cell.

17. The method of claim 16 wherein said cell is obtained by exfoliation.

18. The method of claim 16 wherein said cell is obtained by a PAP smear.

19. A method for detecting a hepadnavirus nucleic acid molecule in a sample, said method comprising:
   amplifying a hepadnavirus nucleic acid molecule, in a biological sample, by use of a pair of primers in a polymerase chain reaction (PCR), to produce amplified nucleic acid material which is in a PCR reaction mix, in the presence of a single stranded nucleic acid probe that is complementary to said amplified nucleic acid material and is immobilized via attachment to the apex of a conical dendron that is attached to a solid surface by the base of said conical dendron,
   completing the last cycle of the PCR to produce amplified nucleic acid material,
   denaturing said amplified nucleic acid material in the presence of said PCR reaction mixture to form a denatured mixture in the presence of the immobilized probe and attached conical dendron,
   allowing the denatured amplified nucleic acid material, within the same PCR reaction mixture, to hybridize to said probe to form a double stranded complex in the presence of said denatured mixture, and
   detecting said complex attached to said solid surface.

20. The method of claim 19 wherein said hepadnavirus is hepatitis B virus (HBV).

21. The method of claim 8 wherein said amplified nucleic acid material comprises a biotin label and said detecting comprises detection of said biotin.

* * * * *

SEQUENCE LISTING

<160> NUMBER OF SEQ ID NOS: 19

<210> SEQ ID NO 1
<211> LENGTH: 7904
<212> TYPE: DNA
<213> ORGANISM: Human papillomavirus type 16

<400> SEQUENCE: 1

```
actacaataa ttcatgtata aaactaaggg cgtaaccgaa atcggttgaa ccgaaaccgg      60
ttagtataaa agcagacatt ttatgcacca aaagagaact gcaatgtttc aggacccaca     120
ggagcgaccc agaaagttac cacagttatg cacagagctg caaacaacta tacatgatat     180
aatattagaa tgtgtgtact gcaagcaaca gttactgcga cgtgaggtat atgactttgc     240
ttttcgggat ttatgcatag tatatagaga tgggaatcca tatgctgtat gtgataaatg     300
tttaaagttt tattctaaaa ttagtgagta tagacattat tgttatagtt tgtatggaac     360
aacattagaa cagcaataca acaaaccgtt gtgtgatttg ttaattaggt gtattaactg     420
tcaaaagcca ctgtgtcctg aagaaaagca aagacatctg gacaaaaagc aaagattcca     480
taatataagg ggtcggtgga ccggtcgatg tatgtcttgt tgcagatcat caagaacacg     540
tagagaaacc cagctgtaat catgcatgga gatacaccta cattgcatga atatatgtta     600
gatttgcaac cagagacaac tgatctctac tgttatgagc aattaaatga cagctcagag     660
gaggaggatg aaatagatgg tccagctgga caagcagaac cggacagagc ccattacaat     720
attgtaacct tttgttgcaa gtgtgactct acgcttcggt tgtgcgtaca aagcacacac     780
gtagacattc gtactttgga agacctgtta atgggcacac taggaattgt gtgccccatc     840
tgttctcaga aaccataatc taccatggct gatcctgcag gtaccaatgg ggaagagggt     900
acgggatgta atggatggtt ttatgtagag gctgtagtgg aaaaaaaaac aggggatgct     960
atatcagatg acgagaacga aaatgacagt gatacaggtg aagatttggt agattttata    1020
gtaaatgata atgattattt aacacaggca gaaacagaga cagcacatgc gttgtttact    1080
gcacaggaag caaaacaaca tagagatgca gtacaggttc taaaacgaaa gtatttggta    1140
gtccacttag tgatattagt ggatgtgtag acaataatat tagtcctaga ttaaaagcta    1200
tatgtataga aaaacaaagt agagctgcaa aaggagatt attgaaagc gaagacagcg    1260 ggtatggcaa tactgaagtg gaaactcagc agatgttaca ggtagaaggg cgccatgaga    1320
ctgaaacacc atgtagtcag tatagtggtg gaagtggggg tggttgcagt cagtacagta    1380
gtggaagtgg gggagagggt gttagtgaaa gacacactat atgccaaaca ccacttacaa    1440
atattttaaa tgtactaaaa actagtaatg caaaggcagc aatgttagca aaatttaaag    1500
agttatacgg ggtgagtttt tcagaattag taagaccatt taaaagtaat aaatcaacgt    1560
gttgcgattg gtgtattgct gcatttggac ttacacccag tatagctgac agtataaaaa    1620
```

```
cactattaca acaatattgt ttatatttac acattcaaag tttagcatgt tcatggggaa    1680
tggttgtgtt actattagta agatataaat gtggaaaaaa tagagaaaca attgaaaaat    1740
tgctgtctaa actattatgt gtgtctccaa tgtgtatgat gatagagcct ccaaaattgc    1800
gtagtacagc agcagcatta tattggtata aacaggtat atcaaatatt agtgaagtgt     1860
atggagacac gccagaatgg atacaaagac aaacagtatt acaacatagt tttaatgatt    1920
gtacatttga attatcacag atggtacaat gggcctacga taatgacata gtagacgata    1980
gtgaaattgc atataaatat gcacaattgg cagacactaa tagtaatgca agtgcctttc    2040
taaaaagtaa ttcacaggca aaaattgtaa aggattgtgc aacaatgtgt agacattata    2100
aacgagcaga aaaaaaacaa atgagtatga gtcaatggat aaaatataga tgtgataggg    2160
tagatgatgg aggtgattgg aagcaaaattg ttatgttttt aaggtatcaa ggtgtagagt    2220
ttatgtcatt tttaactgca ttaaaaagat ttttgcaagg catacctaaa aaaaattgca    2280
tattactata tggtgcagct aacacaggta atcattatt tggtatgagt ttaatgaaat     2340
ttctgcaagg gtctgtaata tgttttgtaa attctaaaag ccattttttg ttacaaccat    2400
tagcagatgc caaaataggt atgttagatg atgctacagt gccctgttgg aactacatag    2460
atgacaattt aagaaatgca ttggatggaa atttagtttc tatggatgta aagcatagac    2520
cattggtaca actaaaatgc cctccattat taattcatc taacattaat gctggtacag     2580
attctaggtg gccttattta cataatagat tggtggtgtt tacatttcct aatgagtttc    2640
catttgacga aaacgaaat ccagtgtatg agcttaatga taagaactgg aaatcctttt     2700
tctcaaggac gtggtccaga ttaagtttgc acgaggacga ggacaaggaa aacgatggag    2760
actctttgcc aacgttttaaa tgtgtgtcag gacaaaatac taacacatta tgaaaatgat    2820
agtacagacc tacgtgacca tatagactat tggaaacaca tgcgcctaga atgtgctatt    2880
tattacaagg ccagagaaat gggatttaaa catattaacc accaagtggt gccaacactg    2940
gctgtatcaa agaataaagc attacaagca attgaactgc aactaacgtt agaaacaata    3000
tataactcac aatatagtaa tgaaaagtgg acattacaag acgttagcct tgaagtgtat    3060
ttaactgcac caacaggatg tataaaaaaa catggatata cagtggaagt gcagtttgat    3120
ggagacatat gcaatacaat gcattataca aactggacac atatatatat ttgtgaagaa    3180
gcatcagtaa ctgtggtaga gggtcaagtt gactattatg gtttatatta tgttcatgaa    3240
ggaatacgaa catattttgt gcagtttaaa gatgatgcag aaaaatatag taaaaataaa    3300
gtatgggaag ttcatgcggg tggtcaggta atattatgtc ctacatctgt gtttagcagc    3360
aacgaagtat cctctcctga aattattagg cagcacttgg ccaaccaccc cgccgcgacc    3420
cataccaaag ccgtcgcctt gggcaccgaa gaaacacaga cgactatcca gcgaccaaga    3480
tcagagccag acaccggaaa cccctgccac accactaagt tgttgcacag agactcagtg    3540
gacagtgctc caatcctcac tgcatttaac agctcacaca aaggacggat taactgtaat    3600
agtaacacta cacccatagt acatttaaaa ggtgatgcta atactttaaa atgtttaaga    3660
tatagattta aaaagcattg tacattgtat actgcagtgt cgtctacatg gcattggaca    3720
ggacataatg taaaacataa aagtgcaatt gttacactta catatgatag tgaatggcaa    3780
cgtgaccaat ttttgtctca agttaaaata ccaaaaacta ttacagtgtc tactggattt    3840
atgtctatat gacaaatctt gatactgcat ccacaacatt actggcgtgc ttttgctttt    3900
gctttgtgtg cttttgtgtg tctgcctatt aatacgtccg ctgcttttgt ctgtgtctac    3960
```

```
atacacatca ttaataatat tggtattact attgtggata cagcagcct ctgcgtttag      4020 gtgttttatt gtatatatta tatttgttta tataccatta tttttaatac atacacatgc      4080
acgcttttta attacataat gtatatgtac ataatgtaat tgttacatat aattgttgta      4140
taccataact tactattttt tcttttttat tttcatatat aatttttttt tttgtttgtt      4200
tgtttgtttt ttaataaact gttattactt aacaatgcga cacaaacgtt ctgcaaaacg      4260
cacaaaacgt gcatcggcta cccaacttta taaaacatgc aaacaggcag gtacatgtcc      4320
acctgacatt atacctaagg ttgaaggcaa aactattgct gaacaaatat tacaatatgg      4380
aagtatgggt gtattttttg gtgggttagg aattggaaca gggtcgggta caggcggacg      4440
cactgggtat attccattgg gaacaaggcc tcccacagct acagatacac ttgctcctgt      4500
aagaccccct ttaacagtag atcctgtggg cccttctgat ccttctatag tttctttagt      4560
ggaagaaact agttttattg atgctggtgc accaacatct gtaccttcca ttcccccaga      4620
tgtatcagga tttagtatta ctacttcaac tgataccaca cctgctatat tagatattaa      4680
taatactgtt actactgtta ctacacataa taatcccact ttcactgacc catctgtatt      4740
gcagcctcca acacctgcag aaactggagg gcattttaca cttttcatcat ccactattag      4800 tacacataat tatgaagaaa ttcctatgga tacatttatt gttagcacaa accctaacac      4860
agtaactagt agcacaccca taccagggtc tcgcccagtg gcacgcctag gattatatag      4920
tcgcacaaca caacaggtta aagttgtaga ccctgctttt gtaaccactc ccactaaact      4980
tattacatat gataatcctg catatgaagg tatagatgtg gataatacat tatattttc       5040 tagtaatgat aatagtatta atatagctcc agatcctgac ttttttggata tagttgcttt     5100 acataggcca gcattaacct ctaggcgtac tggcattagg tacagtagaa ttggtaataa      5160
acaaacacta cgtactcgta gtggaaaatc tataggtgct aaggtacatt attattatga      5220
tttaagtact attgatcctg cagaagaaat agaattacaa actataacac cttctacata      5280
tactaccact tcacatgcag cctcacctac ttctattaat aatggattat atgatattta      5340
tgcagatgac tttattacag atacttctac aaccccggta ccatctgtac cctctacatc      5400
tttatcaggt tatattcctg caaatacaac aattcctttt ggtggtgcat acaatattcc      5460
tttagtatca ggtcctgata tacccattaa tataactgac caagctcctt cattaattcc      5520
tatagttcca gggtctccac aatatacaat tattgctgat gcaggtgact ttatttaca       5580 tcctagttat tacatgttac gaaaacgacg taaacgttta ccatattttt tttcagatgt      5640
ctctttggct gcctagtgag gccactgtct acttgcctcc tgtcccagta tctaaggttg      5700
taagcacgga tgaatatgtt gcacgcacaa acatatatta tcatgcagga acatccagac      5760
tacttgcagt tggacatccc tattttccta ttaaaaaacc taacaataac aaaatattag      5820
ttcctaaagt atcaggatta caatacaggg tatttagaat acatttacct gaccccaata      5880
agtttggttt tcctgacacc tcattttata atccagatac acagcggctg gtttgggcct      5940
gtgtaggtgt tgaggtaggt cgtggtcagc cattaggtgt gggcattagt ggccatcctt      6000
tattaaataa attggatgac acagaaaatg ctagtgctta tgcagcaaat gcaggtgtgg      6060
ataatagaga atgtatatct atggattaca acaaacaca attgtgttta attggttgca      6120
aaccacctat aggggaacac tggggcaaag gatccccatg taccaatgtt gcagtaaatc      6180
caggtgattg tccaccatta gagttaataa acacagttat tcaggatggt gatatggttc      6240
atactggctt tggtgctatg gactttacta cattacaggc taacaaaagt gaagttccac      6300
tggatatttg tacatctatt tgcaaatatc cagattatat taaaatggtg tcagaaccat      6360
```

```
atggcgacag cttatttttt tatttacgaa gggaacaaat gtttgttaga catttatttta    6420
ataggqctgg tactgttggt gaaaatgtac cagacgattt atacattaaa ggctctgggt    6480
ctactgcaaa tttagccagt tcaaattatt ttcctacacc tagtggttct atggttacct    6540
ctgatgccca aatattcaat aaaccttatt ggttacaacg agcacagggc cacaataatg    6600
gcatttgttg gggtaaccaa ctatttgtta ctgttgttga tactacacgc agtacaaata    6660
tgtcattatg tgctgccata tctacttcag aaactacata taaaaatact aactttaagg    6720
agtacctacg acatggggag gaatatgatt tacagtttat ttttcaactg tgcaaaataa    6780
ccttaactgc agacgttatg acatacatac attctatgaa ttccactatt ttggaggact    6840
ggaattttgg tctacaacct cccccaggag gcacactaga agatacttat aggtttgtaa    6900
cccaggcaat tgcttgtcaa aaacatacac ctccagcacc taagaagat gatcccctta    6960
aaaaatacac tttttgggaa gtaaatttaa aggaaaagtt ttctgcagac ctagatcagt    7020
ttccttagg acgcaaattt ttactacaag caggattgaa ggccaaacca aaatttacat    7080
taggaaaacg aaaagctaca cccaccacct catctacctc tacaactgct aaacgcaaaa    7140
aacgtaagct gtaagtattg tatgtatgtt gaattagtgt tgtttgttgt gtatatgttt    7200
gtatgtgctt gtatgtgctt gtaaatatta agttgtatgt gtgtttgtat gtatggtata    7260
ataaacacgt gtgtatgtgt ttttaaatgc ttgtgtaact attgtgtcat gcaacataaa    7320
taaacttatt gtttcaacac ctactaattg tgttgtggtt attcattgta tataaactat    7380
atttgctaca tcctgttttt gttttatata tactatattt tgtagcgcca ggcccatttt    7440
gtagcttcaa ccgaattcgg ttgcatgctt tttggcacaa aatgtgtttt tttaaatagt    7500
tctatgtcag caactatggt ttaaacttgt acgtttcctg cttgccatgc gtgccaaatc    7560
cctgttttcc tgacctgcac tgcttgccaa ccattccatt gttttttaca ctgcactatg    7620
tgcaactact gaatcactat gtacattgtg tcatataaaa taaatcacta tgcgccaacg    7680
ccttacatac cgctgttagg cacatatttt tggcttgttt taactaaccct aattgcatat    7740
ttggcataag gtttaaactt ctaaggccaa ctaaatgtca ccctagttca tacatgaact    7800
gtgtaaaggt tagtcataca ttgttcattt gtaaaactgc acatgggtgt gtgcaaaccg    7860
attttgggtt acacatttac aagcaactta tataataata ctaa                    7904
```

<210> SEQ ID NO 2
<211> LENGTH: 7857
<212> TYPE: DNA
<213> ORGANISM: Human papillomavirus type 18

<400> SEQUENCE: 2

```
attaatactt ttaacaattg tagtatataa aaaagggagt aaccgaaaac ggtcgggacc     60
gaaaacggtg tatataaaag atgtgagaaa cacaccacaa tactatggcg cgctttgagg    120
atccaacacg gcgaccctac aagctacctg atctgtgcac ggaactgaac acttcactgc    180
aagacataga aataacctgt gtatattgca agacagtatt ggaacttaca gaggtatttg    240
aatttgcatt taaagattta tttgtggtgt atagagacag tataccccat gctgcatgcc    300
ataaatgtat agatttttat tctagaatta gagaattaag acattattca gactctgtgt    360
atggagacac attggaaaaa ctaactaaca ctgggttata caatttatta ataaggtgcc    420
tgcggtgcca gaaccgttg aatccagcag aaaaacttag acaccttaat gaaaaacgac    480
gatttcacaa catagctggg cactatagag gccagtgcca ttcgtgctgc aaccgagcac    540
```

```
gacaggaacg actccaacga cgcagagaaa cacaagtata atattaagta tgcatggacc      600
taaggcaaca ttgcaagaca ttgtattgca tttagagccc caaaatgaaa ttccggttga      660
ccttctatgt cacgagcaat taagcgactc agaggaagaa aacgatgaaa tagatggagt     720
taatcatcaa catttaccag cccgacgagc cgaaccacaa cgtcacacaa tgttgtgtat     780
gtgttgtaag tgtgaagcca gaattgagct agtagtagaa agctcagcag acgaccttcg     840
agcattccag cagctgtttc tgaacaccct gtcctttgtg tgtccgtggt gtgcatccca     900
gcagtaagca acaatggctg atccagaagg tacagacggg gagggcacgg gttgtaacgg     960
ctggttttat gtacaagcta ttgtagacaa aaaaacagga gatgtaatat cagatgacga    1020
ggacgaaaat gcaacagaca cagggtcgga tatggtagat tttattgata cacaaggaac    1080
attttgtgaa caggcagagc tagagacagc acaggcattg ttccatgcgc aggaggtcca    1140
caatgatgca caagtgttgc atgttttaaa acgaaagttt gcaggaggca gcacagaaaa    1200
cagtccatta ggggagcggc tggaggtgga tacagagtta agtccacggt tacaagaaat    1260
atctttaaat agtgggcaga aaaggcaaa aaggcggctg tttacaatat cagatagtgg     1320
ctatggctgt tctgaagtgg aagcaacaca gattcaggta actacaaatg gcgaacatgg    1380
cggcaatgta tgtagtggcg gcagtacgga ggctatagac aacgggggca cagagggcaa    1440
caacagcagt gtagacggta caagtgacaa tagcaatata gaaaatgtaa atccacaatg    1500
taccatagca caattaaaag acttgttaaa agtaaacaat aaacaaggag ctatgttagc    1560
agtatttaaa gacacatatg gctatcatt tacagattta gttagaaatt ttaaaagtga    1620 taaaccacg tgtacagatt gggttacagc tatatttgga gtaaacccaa caatagcaga    1680
aggatttaaa acactaatac agccatttat attatatgcc catattcaat gtctagactg    1740
taaatgggga gtattaatat tagccctgtt gcgttacaaa tgtggtaaga gtagactaac    1800
agttgctaaa ggtttaagta cgttgttaca cgtacctgaa acttgtatgt taattcaacc    1860
accaaaattg cgaagtagtg ttgcagcact atattggtat agaacaggaa tatcaaatat    1920
tagtgaagta atgggagaca cacctgagtg gatacaaaga cttactatta tacaacatgg    1980
aatagatgat agcaattttg atttgtcaga aatggtacaa tgggcatttg ataatgagct    2040
gacagatgaa agcgatatgg catttgaata tgccttatta gcagacagca acagcaatgc    2100
agctgccttt ttaaaaagca attgccaagc taaatattta aaagattgtg ccacaatgtg    2160
caaacattat aggcgagccc aaaaacgaca aatgaatatg tcacagtgga tacgatttag    2220
atgttcaaaa atagatgaag ggggagattg gagaccaata gtgcaattcc tgcgatacca    2280
acaaatagag tttataacat tttaggagc cttaaaatca ttttaaaag gaaccccaa     2340 aaaaaattgt ttagtatttt gtggaccagc aaatacagga aaatcatatt ttggaatgag    2400
ttttatacac tttatacaag gagcagtaat atcatttgtg aattccacta gtcatttttg    2460 gttgaaccg ttaacagata ctaaggtggc catgttagat gatgcaacga ccacgtgttg    2520
gacatacttt gatacctata tgagaaatgc gttagatggc aatccaataa gtattgatag    2580
aaagcacaaa ccattaatac aactaaaatg tcctccaata ctactaacca caaatataca    2640
tccagcaaag gataatagat ggccatattt agaaagtaga ataacagtat tgaatttcc     2700 aaatgcattt ccatttgata aaaatggcaa tccagtatat gaaataaatg acaaaaattg    2760
gaaatgtttt tttgaaagga catggtccag attagatttg cacgaggaag aggaagatgc    2820
agacaccgaa ggaaacccctt tcggaacgtt taagttgcgt gcaggacaaa atcatagacc    2880
actatgaaaa tgacagtaaa gacatagaca gccaaataca gtattggcaa ctaatacgtt    2940
```

```
gggaaaatgc aatattcttt gcagcaaggg aacatggcat acagacatta aaccaccagg   3000
tggtgccagc ctataacatt tcaaaaagta aagcacataa agctattgaa ctgcaaatgg   3060
ccctacaagg ccttgcacaa agtcgataca aaaccgagga ttggacactg caagacacat   3120
gcgaggaact atggaataca gaacctactc actgctttaa aaaaggtggc caaacagtac   3180
aagtatattt tgatggcaac aaagacaatt gtatgaccta tgtagcatgg gacagtgtgt   3240
attatatgac tgatgcagga acatgggaca aaaccgctac ctgtgtaagt cacaggggat   3300
tgtattatgt aaaggaaggg tacaacacgt tttatataga atttaaaagt gaatgtgaaa   3360
aatatgggaa cacaggtacg tgggaagtac attttgggaa taatgtaatt gattgtaatg   3420
actctatgtg cagtaccagt gacgacacgg tatccgctac tcagcttgtt aaacagctac   3480
agcacacccc ctcaccgtat tccagcaccg tgtccgtggg caccgcaaag acctacggcc   3540
agacgtcggc tgctacacga cctggacact gtggactcgc ggagaagcag cattgtggac   3600
ctgtcaaccc acttctcggt gcagctcacc tacaggcaa caacaaaaga cggaaactct   3660
gtagtggtaa cactacgcct ataatacatt taaaaggtga cagaaacagt ttaaaatgtt   3720
tacggtacag attgcgaaaa catagcgacc actatagaga tatatcatcc acctggcatt   3780
ggacaggtgc aggcaatgaa aaaacaggaa tactgactgt aacataccat agtgaaacac   3840
aaagaacaaa attttaaat actgttgcaa ttccagatag tgtacaaata ttggtgggat   3900
acatgacaat gtaatacata tgctgtagta ccaatatgtt atcacttatt tttttatttt   3960
gcttttgtgt atgcatgtat gtgtgctgcc atgtcccgct tttgccatct gtctgtatgt   4020
gtgcgtatgc atgggtattg gtatttgtgt atattgtggt aataacgtcc cctgccacag   4080
cattcacagt atatgtattt tgttttttat tgcccatgtt actattgcat atacatgcta   4140
tattgtcttt acagtaattg tataggttgt tttatacagt gtattgtaca ttgtatattt   4200
tgttttatac cttttatgct ttttgtattt ttgtaataaa agtatggtat cccaccgtgc   4260
cgcacgacgc aaacgggctt cggtaactga cttatataaa acatgtaaac aatctggtac   4320
atgtccacct gatgttgttc ctaaggtgga gggcaccacg ttagcagata aaatattgca   4380
atggtcaagc cttggtatat ttttgggtgg acttggcata ggtactggca gtggtacagg   4440
gggtcgtaca gggtacattc cattgggtgg gcgttccaat acagtggtgg atgttggtcc   4500
tacacgtccc ccagtggtta ttgaacctgt gggcccaca gacccatcta ttgttacatt   4560
aatagaggac tccagtgtgg ttacatcagg tgcacctagg cctacgttta ctggcacgtc   4620
tgggtttgat ataacatctg cgggtacaac tacacctgcg gttttggata tcacaccttc   4680
gtctacctct gtgtctattt ccacaaccaa ttttaccaat cctgcatttt ctgatccgtc   4740
cattattgaa gttccacaaa ctggggaggt ggcaggtaat gtatttgttg gtaccccta c   4800
atctggaaca catgggtatg aggaaatacc tttacaaaca tttgcttctt ctggtacggg   4860
ggaggaaccc attagtagta ccccattgcc tactgtgcgg cgtgtagcag gtccccgcct   4920
ttacagtagg gcctaccaac aagtgtcagt ggctaaccct gagtttctta cacgtccatc   4980
ctctttaatt acatatgaca acccggcctt tgagcctgtg gacactacat taacatttga   5040
tcctcgtagt gatgttcctg attcagattt tatggatatt atccgtctac ataggcctgc   5100
tttaacatcc aggcgtggga ctgttcgctt tagtagatta ggtcaacggg caactatgtt   5160
tacccgcagc ggtacacaaa taggtgctag ggttcacttt tatcatgata taagtcctat   5220
tgcaccttcc ccagaatata ttgaactgca gcctttagta tctgccacgg aggacaatga   5280
```

-continued

```
cttgtttgat atatatgcag atgacatgga ccctgcagtg cctgtaccat cgcgttctac      5340
tacctccttt gcattttta aatattcgcc cactatatct tctgcctctt cctatagtaa       5400
tgtaacggtc cctttaacct cctcttggga tgtgcctgta tacacgggtc ctgatattac      5460
attaccatct actacctctg tatggcccat tgtatcaccc acggcccctg cctctacaca      5520
gtatattggt atacatggta cacattatta tttgtggcca ttatattatt ttattcctaa      5580
gaaacgtaaa cgtgttccct atttttttgc agatggcttt gtggcggcct agtgacaata      5640
ccgtatatct tccacctcct tctgtggcaa gagttgtaaa taccgatgat tatgtgactc      5700
ccacaagcat attttatcat gctggcagct ctagattatt aactgttggt aatccatatt      5760
ttagggttcc tgcaggtggt ggcaataagc aggatattcc taaggtttct gcataccaat      5820
atagagtatt tagggtgcag ttacctgacc caaataaatt tggtttacct gatactagta      5880
tttataatcc tgaaacacaa cgtttagtgt gggcctgtgc tggagtggaa attggccgtg      5940
gtcagccttt aggtgttggc cttagtgggc atccatttta taataaatta gatgacactg      6000
aaagttccca tgccgccacg tctaatgttt ctgaggacgt tagggacaat gtgtctgtag      6060
attataagca gacacagtta tgtattttgg gctgtgcccc tgctattggg gaacactggg      6120
ctaaaggcac tgcttgtaaa tcgcgtcctt tatcacaggg cgattgcccc cctttagaac      6180
ttaaaaacac agttttggaa gatggtgata tggtagatac tggatatggt gccatggact      6240
ttagtacatt gcaagatact aaatgtgagg taccattgga tatttgtcag tctatttgta      6300
aatatcctga ttatttacaa atgtctgcag atccttatgg ggattccatg tttttttgct      6360 tacgcgtga gcagcttttt gctaggcatt tttggaatag agcaggtact atgggtgaca      6420
ctgtgcctca atccttatat attaaaggca caggtatgcc tgcttcacct ggcagctgtg      6480
tgtattctcc ctctccaagt ggctctattg ttacctctga ctcccagttg tttaataaac      6540
catattggtt acataaggca cagggtcata caatggtgt tgctggcat aatcaattat      6600 ttgttactgt ggtagatacc actcccagta ccaatttaac aatatgtgct tctacacagt      6660
ctcctgtacc tgggcaatat gatgctacca aatttaagca gtatagcaga catgttgagg      6720
aatatgattt gcagtttatt tttcagttgt gtactattac tttaactgca gatgttatgt      6780
cctatattca tagtatgaat agcagtattt tagaggattg gaactttggt gttccccccc      6840
ccccaactac tagtttggtg gatacatatc gttttgtaca atctgttgct attacctgtc      6900
aaaaggatgc tgcaccggct gaaaataagg atccctatga taagttaaag ttttggaatg      6960
tggatttaaa ggaaaagttt tcttttagact tagatcaata tcccccttgga cgtaaattt       7020 tggttcaggc tggattgcgt cgcaagccca ccataggccc tcgcaaacgt tctgctccat      7080
ctgccactac gtcttctaaa cctgccaagc gtgtgcgtgt acgtgccagg aagtaatatg      7140
tgtgtgtgta tatatatata catctattgt tgtgtttgta tgtcctgtgt ttgtgtttgt      7200
tgtatgattg cattgtatgg tatgtatggt tgttgttgta tgttgtatgt tactatattt      7260
gttggtatgt ggcattaaat aaaatatgtt ttgtggttct gtgtgttatg tggttgcgcc      7320
ctagtgagta acaactgtat ttgtgtttgt ggtatgggtg ttgcttgttg ggctatatat      7380
tgtcctgtat ttcaagttat aaaactgcac accttacagc atccatttta tcctacaatc      7440
ctccattttg ctgtgcaacc gatttcggtt gcctttggct tatgtctgtg gttttctgca      7500
caatacagta cgctggcact attgcaaact ttaatctttt gggcactgct cctacatatt      7560
ttgaacaatt ggcgcgcctc tttggcgcat ataaggcgca cctggtatta gtcatttcc       7620 tgtccaggtg cgctacaaca attgcttgca taactatatc cactccctaa gtaataaaac      7680
```

```
tgcttttagg cacatatttt agtttgtttt tacttaagct aattgcatac ttggcttgta    7740
caactacttt catgtccaac attctgtcta cccttaacat gaactataat atgactaagc    7800
tgtgcataca tagtttatgc aaccgaaata ggttgggcag cacatactat acttttc       7857
```

```
<210> SEQ ID NO 3
<211> LENGTH: 29
<212> TYPE: DNA
<213> ORGANISM: Artificial Sequence
<220> FEATURE:
<223> OTHER INFORMATION: Probe that hybridizes to human papillomavirus
      type 16

<400> SEQUENCE: 3
ctctgggtct actgcaaatt tagccagtt                                       29

<210> SEQ ID NO 4
<211> LENGTH: 29
<212> TYPE: DNA
<213> ORGANISM: Artificial Sequence
<220> FEATURE:
<223> OTHER INFORMATION: PCR primer

<400> SEQUENCE: 4
gatggtgata tggtwsatac aggmtwtgg                                       29

<210> SEQ ID NO 5
<211> LENGTH: 29
<212> TYPE: DNA
<213> ORGANISM: Artificial Sequence
<220> FEATURE:
<223> OTHER INFORMATION: PCR primer

<400> SEQUENCE: 5
gmrtcagagg ttacmataga rccactwgg                                       29

<210> SEQ ID NO 6
<211> LENGTH: 29
<212> TYPE: DNA
<213> ORGANISM: Artificial Sequence
<220> FEATURE:
<223> OTHER INFORMATION: PCR primer

<400> SEQUENCE: 6
gatggtgata tggtwsatac tggmtwtgg                                       29

<210> SEQ ID NO 7
<211> LENGTH: 29
<212> TYPE: DNA
<213> ORGANISM: Artificial Sequence
<220> FEATURE:
<223> OTHER INFORMATION: PCR primer

<400> SEQUENCE: 7
gmrtcagagg taacmataga rccactwgg                                       29

<210> SEQ ID NO 8
<211> LENGTH: 23
<212> TYPE: DNA
<213> ORGANISM: Artificial Sequence
<220> FEATURE:
<223> OTHER INFORMATION: Probe that hybridizes to human papillomavirus
      type 18

<400> SEQUENCE: 8
```

```
cacaggtatg cctgcttcac ctg                                            23

<210> SEQ ID NO 9
<211> LENGTH: 30
<212> TYPE: DNA
<213> ORGANISM: Artificial Sequence
<220> FEATURE:
<223> OTHER INFORMATION: Probe that hybridizes to a reverse primer

<400> SEQUENCE: 9
tttacaccta gtggctctat ggtgtcctct                                     30

<210> SEQ ID NO 10
<211> LENGTH: 23
<212> TYPE: DNA
<213> ORGANISM: Artificial Sequence
<220> FEATURE:
<223> OTHER INFORMATION: Probe that hybridizes to human papillomavirus
      type 53

<400> SEQUENCE: 10
acccgccccc tagctctgta tat                                            23

<210> SEQ ID NO 11
<211> LENGTH: 22
<212> TYPE: DNA
<213> ORGANISM: Artificial Sequence
<220> FEATURE:
<223> OTHER INFORMATION: Probe that hybridizes to human papillomavirus
      type 58

<400> SEQUENCE: 11
ctggaaaact tggcgaggct gt                                             22

<210> SEQ ID NO 12
<211> LENGTH: 18
<212> TYPE: DNA
<213> ORGANISM: Artificial Sequence
<220> FEATURE:
<223> OTHER INFORMATION: Probe that hybridizes to human papillomavirus
      type 6

<400> SEQUENCE: 12
aaatcgcacg tctgtagg                                                  18

<210> SEQ ID NO 13
<211> LENGTH: 25
<212> TYPE: DNA
<213> ORGANISM: Artificial Sequence
<220> FEATURE:
<223> OTHER INFORMATION: Probe that hybridizes to human papillomavirus
      type 11

<400> SEQUENCE: 13
tgcctgatga cctgttggta aaagg                                          25

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14
tggccaaaat tcgcagtccc                                                20
```

```
<210> SEQ ID NO 15
<211> LENGTH: 27
<212> TYPE: DNA
<213> ORGANISM: Artificial Sequence
<220> FEATURE:
<223> OTHER INFORMATION: PCR primer

<400> SEQUENCE: 15
tgacatactt tccaatcaat aggtcta                                              27

<210> SEQ ID NO 16
<211> LENGTH: 25
<212> TYPE: DNA
<213> ORGANISM: Artificial Sequence
<220> FEATURE:
<223> OTHER INFORMATION: Probe that hybridizes to hepatitus B virus

<400> SEQUENCE: 16 attttctttty gtctytgggt ataca                                               25

<210> SEQ ID NO 17
<211> LENGTH: 23
<212> TYPE: DNA
<213> ORGANISM: Artificial Sequence
<220> FEATURE:
<223> OTHER INFORMATION: Probe that hybridizes to hepatitis B virus

<400> SEQUENCE: 17
tttctttygt ctytgggtgt aca                                                  23

<210> SEQ ID NO 18
<211> LENGTH: 20
<212> TYPE: DNA
<213> ORGANISM: Artificial Sequence
<220> FEATURE:
<223> OTHER INFORMATION: Probe that hybridizes to hepatitis B virus

<400> SEQUENCE: 18
ctttygtcty tgggtgtgca                                                      20

<210> SEQ ID NO 19
<211> LENGTH: 22
<212> TYPE: DNA
<213> ORGANISM: Artificial Sequence
<220> FEATURE:
<223> OTHER INFORMATION: Probe that hybridizes to hepatitis B virus

<400> SEQUENCE: 19
ttctttygtc tytgggtatg ca                                                   22
```